(12) United States Patent
Faustman

(10) Patent No.: US 6,984,380 B1
(45) Date of Patent: Jan. 10, 2006

(54) TREATMENT OF DISEASES INVOLVING FAULTY MHC CLASS I ANTIGEN COMPLEX PRESENTATION

(75) Inventor: Denise Faustman, Weston, MA (US)

(73) Assignee: Denise L. Faustman, Weston, MA (US)

( * ) Notice: Subject to any disclaimer, the term of this patent is extended or adjusted under 35 U.S.C. 154(b) by 0 days.

(21) Appl. No.: 08/455,022

(22) Filed: May 31, 1995

Related U.S. Application Data

(60) Division of application No. 08/096,941, filed on Jul. 14, 1993, now Pat. No. 5,538,854, which is a continuation-in-part of application No. 07/810,517, filed on Dec. 19, 1991, now abandoned, which is a continuation-in-part of application No. 07/739,878, filed on Aug. 2, 1991, now abandoned.

(51) Int. Cl.
*A61K 48/00* (2006.01)
*A61K 38/00* (2006.01)
*C12N 5/00* (2006.01)
*C12N 15/63* (2006.01)
*C12N 15/75* (2006.01)

(52) U.S. Cl. ................ 424/93.21; 424/93.2; 424/193.1; 435/320.1; 435/325; 435/455

(58) Field of Classification Search .............. 424/193.1, 424/93.2, 93.21; 435/325, 455, 320.1; 512/44, 512/2

See application file for complete search history.

(56) References Cited

U.S. PATENT DOCUMENTS 4,946,674 A   8/1990   von Eichborn et al.
5,635,363 A   6/1997   Altman et al.

FOREIGN PATENT DOCUMENTS

WO    WO 90/10016    9/1990

OTHER PUBLICATIONS

Jacob et al. (1990) PNAS, vol. 87, 968–972.*
Eck and Wilson (1996) Pharm. Basis of Therapeutics. Chapter 5, pp. 77–101.*
Ledley (1996) Pharm. Res., vol. 13, 1595–1614.*
Ledley, (1991) Human Gene Therapy, vol. 2, 77–83.*
Verma et al. (1997) Nature, vol. 389, 239–242, 1997.*
Marshall et al. (1995) Science, vol. 269, 1050–1055, 1995.*
Orkin et al. (1995) "Report and Recommendations of the Panel . . . ", 1995.*
Kalden et al. (1998) Advances in Immunology, vol. 68, 396–401, 1997.*
Bikoff et al Nature 354 : 235, 1991.*
Spies et al Nature 348 : 744, 1990.*
Festenstein et al Nature 322 64, 1986.*
Trowsdale et al Nature 348 741, 1990.*
Selden et al Seminars in Medicine 317(17) : 1067, 1987.*
Spies et al Nature, 355: 644, 1992.*
Van Bleek et al Nature 348 213, 1990.*
Berkos et al., File Server STN Karlsruhe, File Medline Abstract No. 90231955, *Probl. Endokrinol.*, (Mosk), 36(1): 3–8 (Jan.–Feb. 1990).
Bikoff et al., *Nature*, 354: 235–238 (1991).
Cohen et al., *Immunol. Rev.*, 85: 87–105 (1985).
Faustman et al., *Diabetes*, 38: 1462–1468 (1989).
Festenstein et al., *Nature*, 322: 64–67 (1986).
Foulis et al., *Diabetes*, 35: 1215–1224 (1986).
Gony et al., *Tissue Antigens*, 31: 229–234 (1988).
Hattori et al., *Science*, 231: 733–735 (1986).
Kelly et al., *Nature*, 353: 667–668 (1991).
Konekov et al., File Server STN Karlsruhe, Medline Abstract No. 88278232, *Ter. Arkh.*, 60(4): 86–89 (1988).
Lawlor et al., *Annu. Rev. Immunol.*, 8: 23–63 (1990).
Leiter et al., *Clin. Immunol. & Immunopath.*, 59:323–334 (1991).
Madden et al., *Nature*, 353: 321–325 (1991).
Miller et al., *Immunol. Today*, 10(2): 53–57 (1989).
Raum et al., *J. Clin. Invest.*, 74: 449–454 (1984).
Rossini et al., *J. Clin. Invest.*, 74: 39–46 (1984).
Rudensky et al., *Nature*, 353:622–627 (1991).
Selden et al., *Seminars in Medicine*, 317(17) 1067–1076 (1987).
Serreze et al., *J. Immunol.*, 140: 3801–3807 (1988).
Spies et al., *Nature*, 351: 323–324 (1991).
Tananov et al., File Biosis Abstract No. 82:259448, *Probl. Gematol. Pereliv. Krovi.*, 26(1): 8–12 (1981).
Trowsdale et al., *Nature*, 348: 741–744 (1990).
Van Bleek et al., *Nature*, 348: 213–216 (1990).
Amrani et al., *Nature*, 406(6767): 739–742 (2000).
Bouvier et al., *Science*, 265: 398–402 (1994).
Chang et al., *J. Immunol.*, 137: 2853–2856 (1986).
Collins et al., *PNAS USA*, 83: 446–450 (1986).
Eisenbarth & Kotzin, *J. Clin. Invest.*, 111(2): 179–181 (2003).
Ferlin et al., *Current Opinion in Immunology*, 12: 670–675 (2003).
Pujol–Borrell et al., *Nature*, 326: 304–306 (1987).

* cited by examiner

*Primary Examiner*—Anne Marie S. Wehbe
(74) *Attorney, Agent, or Firm*—Leon R. Yankwich; Yankwich & Associates, P.C.

(57) ABSTRACT

Methods of treating autoimmune diseases, such as diabetes, characterized by faulty MHC class I antigen complex presentation are disclosed which involve exposure of the immune system of an individual susceptible to such disease to correctly associated MHC class I antigen complexes. Such treatment may involve obtaining cells from the individual, treating the cells to correct faulty MHC class I antigen presentation, then reinfusing the treated cells. Alternatively, syngeneic or haplotype-matched allogeneic lymphoid cells expressing normal levels of MHC class I antigen complexes may be used or intact MHC class I antigen complexes isolated from such lymphoid cells may be used in such treatment.

60 Claims, 12 Drawing Sheets

Column 1: High risk "prediabetics" (n=6)
Column 2: Diabetic twins (n=4)
Column 3: Long term type 1 diabetics (n=20)
Column 4: EBV transformed cell lines from long term diabetics (n=10)
Column 5: Controls (n=39)
Column 6: Low risk "prediabetics" (n=5)
Column 7: Non-diabetic twins (n=4)
Column 8: First degree relatives (n=10)
Column 9: EBV transformed cell lines from controls (n=10)

TREATMENT OF DISEASES INVOLVING FAULTY MHC CLASS I ANTIGEN COMPLEX PRESENTATION

CROSS REFERENCE TO RELATED APPLICATIONS

This application is a division of U.S. application Ser. No. 08/096,941, filed Jul. 14, 1993, now U.S. Pat. No. 5,538,854, which is a continuation-in-part of U.S. application Ser. No. 07/810,517, filed Dec. 19, 1991 and now abandoned, which is a continuation-in-part of U.S. application Ser. No. 07/739,878, filed Aug. 2, 1991 and now abandoned.

BACKGROUND OF THE INVENTION

This invention relates to testing and treatment of autoimmune diseases such as type I diabetes. The invention takes advantage of a link have discovered between type I diabetes and major histocompatibility complex (MHC) class I molecules, or HLA class I molecules, as they will be referred to herein.

T-lymphocytes recognize self or foreign proteins in the binding groove of HLA, resulting in HLA-restricted immune responses. Peptides in the extracellular compartment are taken up by antigen presenting cells by endocytosis and subsequently are presented as peptides in association with HLA Class II complexes. These HLA Class II-peptide complexes are recognized by CD4+ helper cells. In contrast, endogenously synthesized antigens, or "self peptides", are transported into the endoplasmic reticulum where they preferentially bind to HLA class I and these HLA-I-peptide complexes are subsequently recognized by CD8+ suppressor or cytotoxic T-cells. HLA class I expression is normally universally present on all cells.

Recently, a series of experiments have identified transmembrane transporter genes involved in the process of transportation of cytosolic peptides into the endoplasmic reticulum, and mapping studies have localized their chromosomal location within the HLA class II region. These peptide supply factor genes (also known as ATP-dependent transporter protein-encoding genes, Tap-1 and Tap-2), are members of the multidrug resistant family of transporters and are highly conserved between species (e.g., see Monaco, *Immunology Today* 13:173–179, 1992). Their identification has been feasible by a series of induced mutant cell lines which lack surface HLA class I (i.e., do not "present" HLA class I) by virue of deletions in either or both of the endogenous Tap-1 and Tap-2 genes (Monaco et al., *Science* 250:1723–1726, 1990; Deverson et al., *Nature* 348:738–741, 1990; Trowsdale et al., *Nature* 348:741–744, 1990; Spies et al., *Nature* 348:744–747, 1990).

Type I diabetes is an autoimmune disease characterized by T-cell mediated destruction of the beta cells in the islets of Langerhans, accompanied by an immune response to a diversity of self peptides. Similar to other autoimmune diseases, IDDM has a genetic predisposition. In the absence of an identified specific gene abnormality, the strongest genetic associations have been between IDDM and genes encoding the HLA class II polypeptides (Todd et al., *Nature* 329:599–604; Thomson et al., *Am. J. Hum. Genet.* 43:799–816; Busch et al., *Expl. J. Med.* 322:1836–1841). Similar linkage has been shown for other autoimmune diseases, including Graves' disease, Hashimoto's thyroiditis systemic lupus erythematosis and autoimmune adrenal insufficiency (Moccs et al., *N. Expl. J. Med.* 399:133; Sveigaard et al., *Immunol. Rev.* 70:193–218; Macharen et al., *J. Clin. Endocrin.* 62:455–459). The strong association between autoimmune disease and HLA class II genes has suggested that abnormalities in HLA class II gene products play a central pathogenetic role in autoimmune diseases.

Humans at risk for type I diabetes can be identified years prior to hyperglycemia by the abnormal occurrence of autoantibodies to insulin, islet cells, glutamic acid decarboxylase, as well as many other autologous proteins. The autoantibody patterns predict eventual disease progression and/or risk. A recent analysis of "prediabetics" as well as discordant diabetic type I identical twins revealed a T-cell developmental defect controlled by abnormal autologous presentation of self antigens which was predictive of disease progression.

SUMMARY OF THE INVENTION

I have discovered that type I diabetes and other autoimmune diseases in man and mouse are accompanied by faulty expression or function of HLA class I molecules on the cell surface which is associated with impaired antigen presentation. The T-cells of the diabetic respond to self antigens as if they were foreign antigens, mediating a defective development of self tolerance. I propose that this defect underlies beta cell autoimmunity, much as abolition of HLA class I expression by beta microglobulin gene deletion in the mouse results in hyperglycemia due to a lymphocyte-mediated insulitis. My evidence suggests that the faulty low expression of HLA class I on the cell surface in the human type I diabetic is due to mutant genes in one or more of the proteins involved in presentation of proteins or peptide fragments thereof on the cell surface by complexation with class I molecules. This failure of patients with autoimmune diseases to properly present tolerance-inducing self antigens can be due to, for example, mutations in a class I gene, in one or more of the peptide transporter genes, or in one or more of the genes encoding the proteosomes responsible for cutting up ("processing") self-proteins for transport to the cell surface for complexation and presentation with HLA class I.

The discovery provides the basis for new tests for autoimmune diseases based on faulty HLA class I presentation, and in addition provides new methods for inducing tolerance to any protein antigen, all based on presenting the antigen to the patient bound to HLA class I.

Accordingly, the invention provides, in a first aspect, a method for testing a mammal, e.g., a human patient, for predisposition to develop an autoimmune disease, by measuring HLA class I expression on cells, e.g., B lymphocytes, of the mammal, a decreased level of HLA I on the cell surface indicating such predisposition. The autoimmune disease is preferably type I diabetes, but can also be systemic lupus erythmatosis (SLE), rheumatoid arthritis, Graves disease, hypoparathyroidism, hypothyroidism, multiple sclerosis, Addison's disease, Celiac disease, Sicca syndrome, Addison's, Myasthenia gravis, Idiopathic mantraneous nephropathy, Optic neuritis, Goodpasteur's Syndrome, Pemphigus, Hashimoto's thyroiditis, pernicious anemia, or ankylosing spondylitis.

In a related aspect, the invention provides a method for testing a mammal for predisposition to develop an autoimmune disease by first obtaining a biological sample from the mammal, and then determining, for that sample, whether there is a defect in or deletion of a gene encoding a component of class HLA class I or a protein which is involved in the processing or transport of endogenous proteins into the endoplasmic reticulum for complexation with HLA class I molecules, or a protein involved in one of the other steps necessary for HLA class I self-antigen presentation on the cell surface. In preferred embodiments of this method, the mammal is a human fetus, and the protein is an ATP-dependent transporter protein (i.e., tap-1 or tap-2) or a proteosome or component thereof (e.g., LMP-1, LMP-2; Glynne et al., Nature 353:357–360; Kelly et al., Nature 353:667–668). The determination of a defective or deleted gene can be carried out in any conventional manner, such as by Western blot analysis, mRNA Northern blot analysis, cell surface protein phenotyping, or restriction fragment length polymorphism (RFLP) analysis, single-stranded chain polymorphism, denaturing gel electrophoresis, or polymerase chain-reaction (PCR).

My discovery also provides the basis for a method of treating a mammal such as a human patient to inhibit development of an autoimmune disease; preferably such treatment is carried out at an early stage, when tolerance is most easily induced. The method involves increasing the amount of HLA class I complexed with self-antigen presented on circulating cells in the mammal, the proper presentation of self-antigens on cells of the mammal thus increasing self-tolerance and decreasing the tendency to develop the autoimmune disease.

One method of achieving this is to increase the amount of HLA class I complexed with self-antigen presented on circulating cells of the mammal. This increase in HLA class I presentation can be accomplished in a variety of ways. In one preferred embodiment, the mammal is treated with cells which present HLA class I bound to endogenous proteins or fragments thereof. These cells can be autologous cells, e.g., the patient's lymphocytes (e.g., B cells or macrophages) which are transfected with DNA encoding one or more of the proteins involved in the processing or transport of endogenous proteins into the endoplasmic reticulum for HLA class I complexation or transport and processing of this complex for a successful journey to the cell surface; these proteins are preferably the ATP-dependent transporter proteins including Tap-1 and Tap-2 (formerly known as RING 3, RING 4, RING 11, HAM 1, HAM 2, Mtp 1, Mtp 2, or Y 3), which demonstrate a high level of homology between species, or the cutting proteins (the proteosome complex) responsible for processing endogenous peptides. The proteosome complex is a large (approximately 250,000 mw) assembly of enzymatically active fragments which process self-proteins, cutting them into pieces generally between about 6 and 14 amino acids in length, so that those fragments can enter the endoplasmic reticulum for transport to the surface for complexation with class I. The proteosome genes are linked to HLA class II, and are described, e.g. in Kelly et al., Nature 353:667–668, 1991. Alternatively, the HLA class-I presenting cells can be obtained from another human (preferably one who has been type-matched).

Another method of increasing the amount of HLA class I capable of presenting self-peptides on the surface of circulating cells of the patient is to administer to the patient or the patient's cells in culture a substance or immunostimulant which produces an increase in HLA class I expression; such substances include the interferons, e.g., a beta- and gamma-interferon, interleukins, and toxoids, e.g., diphtheria toxoid, tumor necrosis factor, BCG, and pertussis toxoid. Infection with a virus or bacterium which stimulates HLA class I presentation is another method which can be employed.

An alternative strategy for increasing the level of cells which present self-complexed with HLA class I is to administer to the mammal the self-antigen or fragment(s) thereof which forms a complex with class I on the surface of a cell, to both stabilize class I and present the antigen to the immune system of the mammal. Preferably, the antigen is a peptide fragment of a protein; more preferably the peptides are 6 to 14 amino acids long, the size range of peptide fragments known to complex with class I; and most preferably the peptide is 9 amino acids long, the optimal length for class I complexation. In a preferred embodiment, the mammal is adminstered a mixture of peptide fragments of a protein. The peptide(s) can be administered orally or intravenously, or cells from the mammal can be incubated with the peptide(s) and then reinfused into the mammal.

The discovery of the role of class I in induction of self-tolerance can make possible the induction of tolerance in a patient to any protein, whether self or exogenous; induction of tolerance is achieved by administering to the patient either cells on which peptide fragments of the protein to which tolerance is to be induced are presented bound to HLA class I, or the antigen-class I complex itself. This method can be used, e.g., where the patient is the recipient of an allograft such as a heart or kidney from another patient, or even from another species. In one embodiment, the method involves transfecting HLA class I-presenting cells, preferably autologous cells such as the patient's B cells, with DNA encoding the protein to which tolerance is to be induced, and then introducing those cells into the patient, where self-tolerance will be induced by virtue of HLA class I presentation of the protein.

Other features and advantages of the invention will be apparent from the following description of the preferred embodiments thereof, and from the claims.

DETAILED DESCRIPTION

The drawings are first described.

DRAWINGS

Figure 10A:
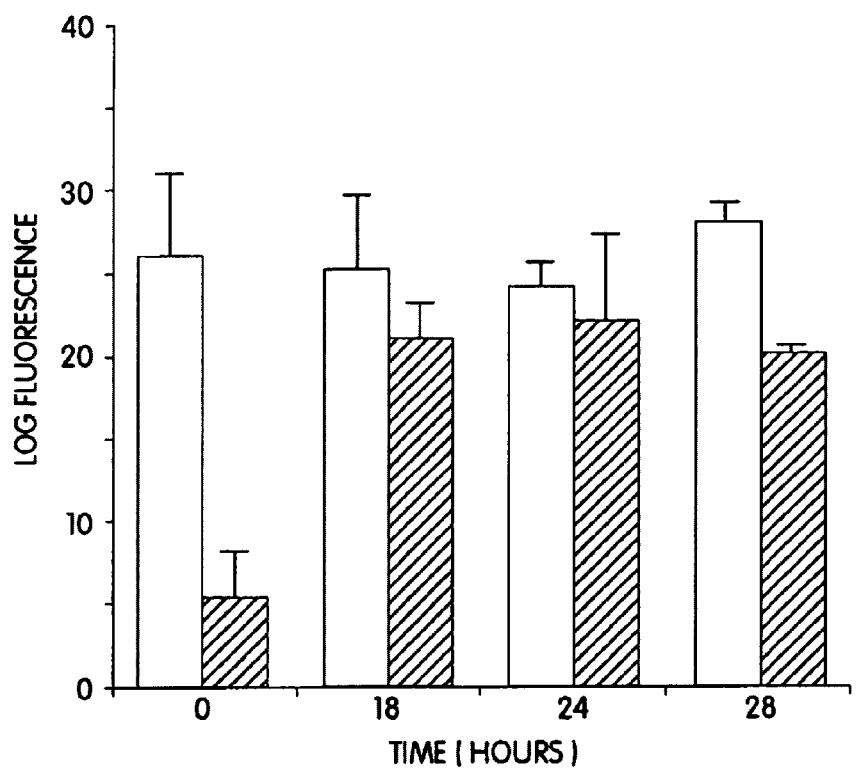

FIG. 10A is a bar graph showing the effect of low temperature on surface expression of class I molecules by lymphocytes from female NOD mice. NOD ($K^d$, $D^b$) (striped bars) and B10.D2 (R103) ($K^d$, $D^b$) (solid bars) splenocytes were cultured for various times at 28° C. The data represent lymphocyte mean fluorescence.

Figure 10B:
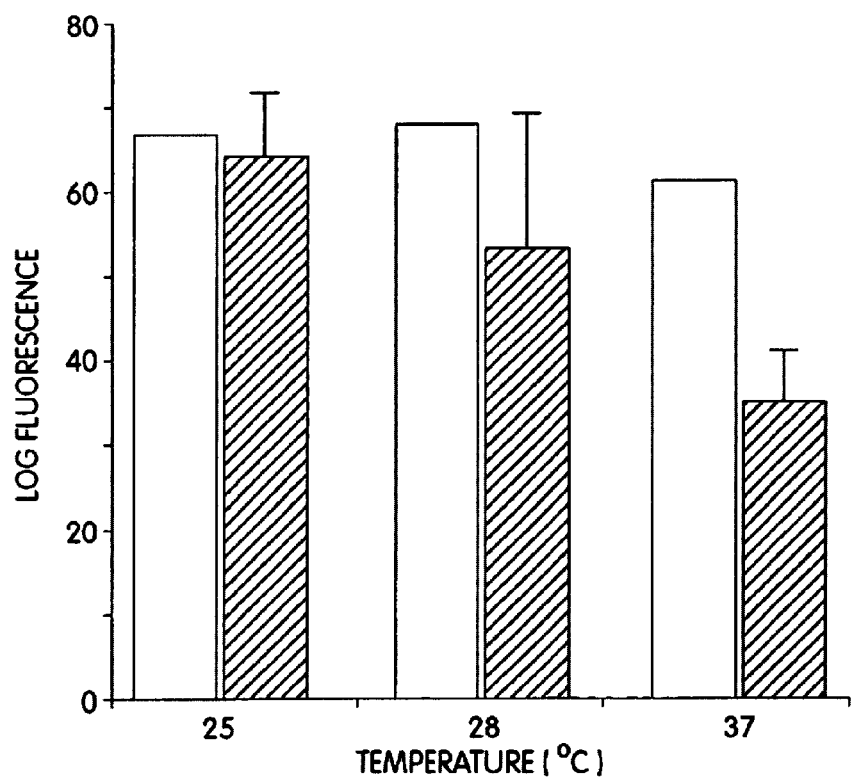

FIG. 10B is a bar graph showing the effect of low temperature on surface expression of class I molecules by macrophages from female NOD mice. NOD ($K^d$, $D^b$) (striped bars) and B10.D2 (R103) ($K^d$, $D^b$) (solid bars) splenocytes were cultured at 25, 28, or 37° C. for 24 hours prior to quantitation of surface $K^d$ expression. The data represents macrophage mean fluorescence.

Figure 11A:
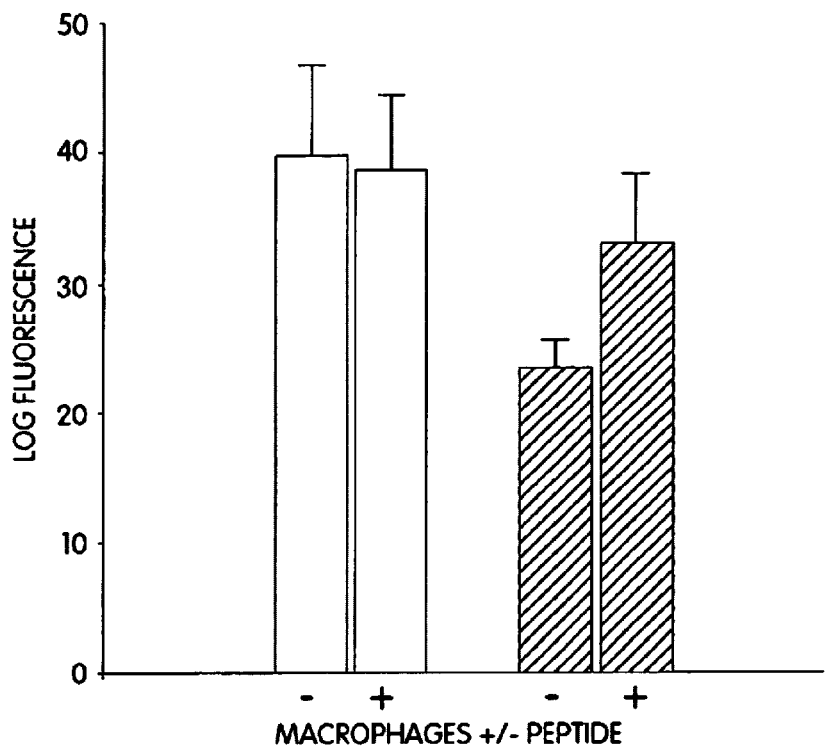

FIG. 11A is a bar graph showing the effect of exogenous synthetic peptide on macrophage surface expression of class I molecules. Control B10.D2 (R103) splenocytes (solid bars) or NOD splenocytes (striped bars) from females were cultured in serum-containing medium at 37° C. with (+) or without (−) $K^d$-specific peptide (480 μM) for 5 hours, and then analyzed by FACS with anti-$K^d$ antibody. The y axis represents log fluorescence for splenocytes with a gate on the large monocyte subpopulation. Comparable data were obtained for a gate on lymphocytes.

Figure 11B:
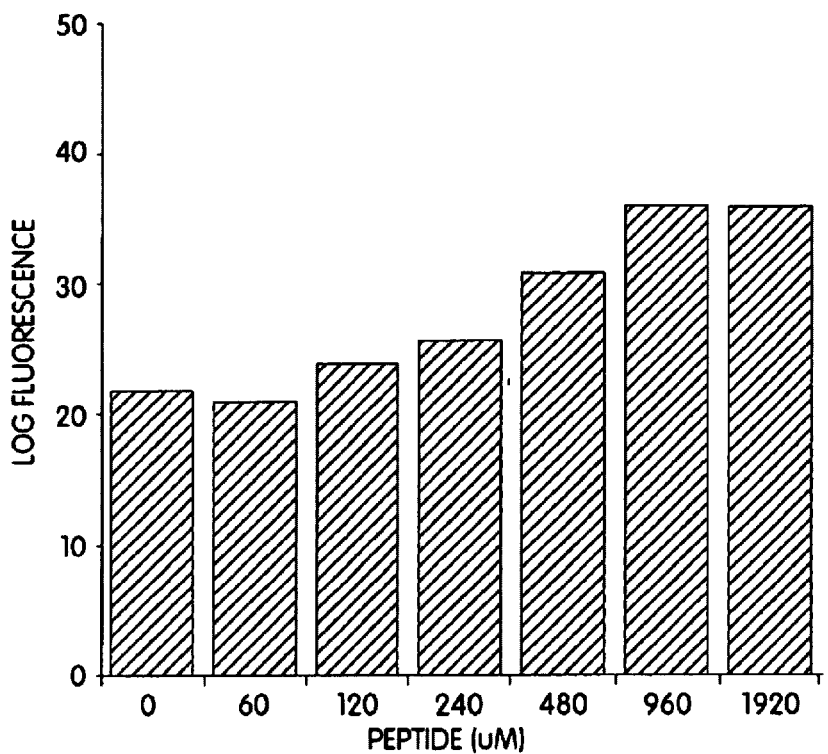

FIG. 11B is a bar graph showing the effect of various concentrations of $K^d$-specific peptide on expression of class I molecules in splenocytes from female NOD mice.

Figure 12:
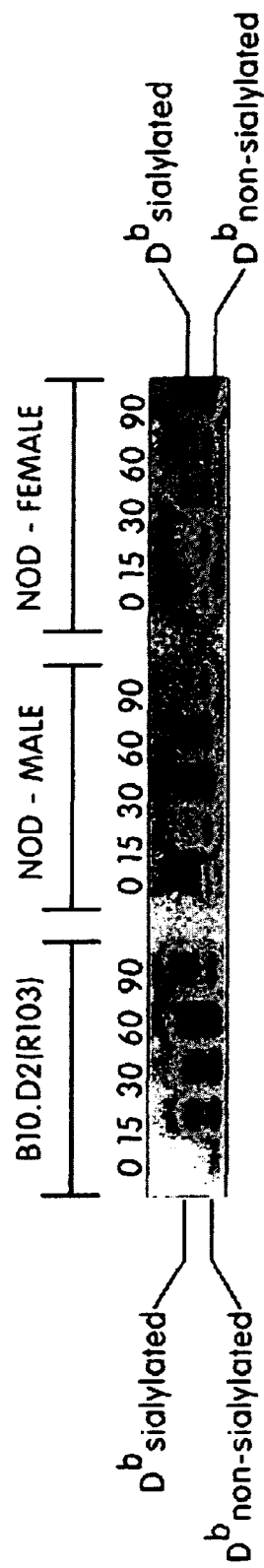

FIG. 12 is an autoradiograph of an SDS-polyacrylamide gel of immunoprecipitates obtained from control B10.D2 (R103), male NOD and female NOD splenocytes subjected to [$^{35}S$]-methionine pulse-chase. The positions of sialylated and nonsialylated $D^b$ are indicated. Data are from single representative mice; the experiment was performed eight times with identical results.

There first are described experiments demonstrating that prediabetic and diabetic mice and humans have decreased levels of conformationally correct HLA class I on the cell surface.

"Prediabetic" and Diabetic NOD Mice and Humans have Decreased HLA Class I Expression Using cell surface phenotyping with an HLA class I-specific monoclonal antibody (W6/32) the peripheral blood lymphocytes from six high risk prediabetics whose serum contained autoantibodies to both insulin and islets; four diabetic twins; and twenty long-term diabetics were assayed for HLA class I expression. The human lymphocytes were prepared for immunofluorescence by standard techniques using a ficol gradient. Flow cytometry (FACS) was carried out with a gate set which excluded remaining red blood cells and debris and which included T cells, B cells, and macrophages. HLA class I expression was also measured in ten Epstein-Barr virus-transformed B cell lines taken from long-term type I diabetics, and several other groups of patients. virus-transformed B cell lines taken from long-term type I diabetics, and several other groups of patients.

Figure 1:
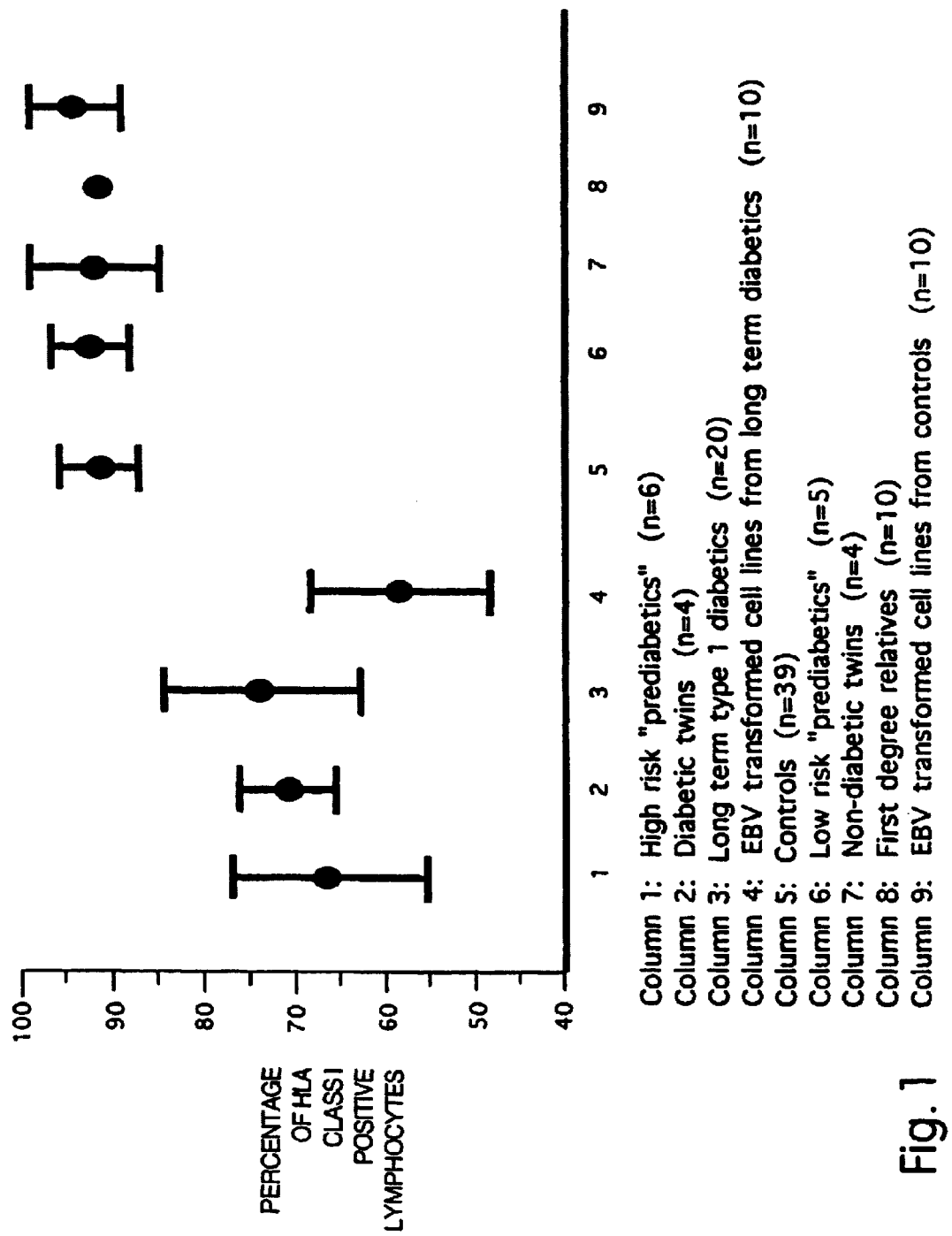
FIG. 1 is a graph showing relative HLA class I on lymphocytes from diabetic and control individuals.

Referring to FIG. 1, HLA class I expression was significantly reduced in all six high risk diabetics, all four diabetic twins, and nineteen of twenty long-term diabetics, and was reduced as well in all ten of the EBV-transformed B cell lines from long-term diabetics.

In marked contrast, all five low-risk prediabetics (i.e., those with insulin autoantibodies, but not islet autoantibodies); four non-diabetic discordant type I twins; ten first-degree relatives; thirty-nine controlled individuals; and ten EBV-transformed cell lines from normal subjects demonstrated normal levels of HLA class I antigen expression; these levels were significantly higher than the other groups. The twin results demonstrate that class I surface expression can be independent of genotype.

Figure 2:
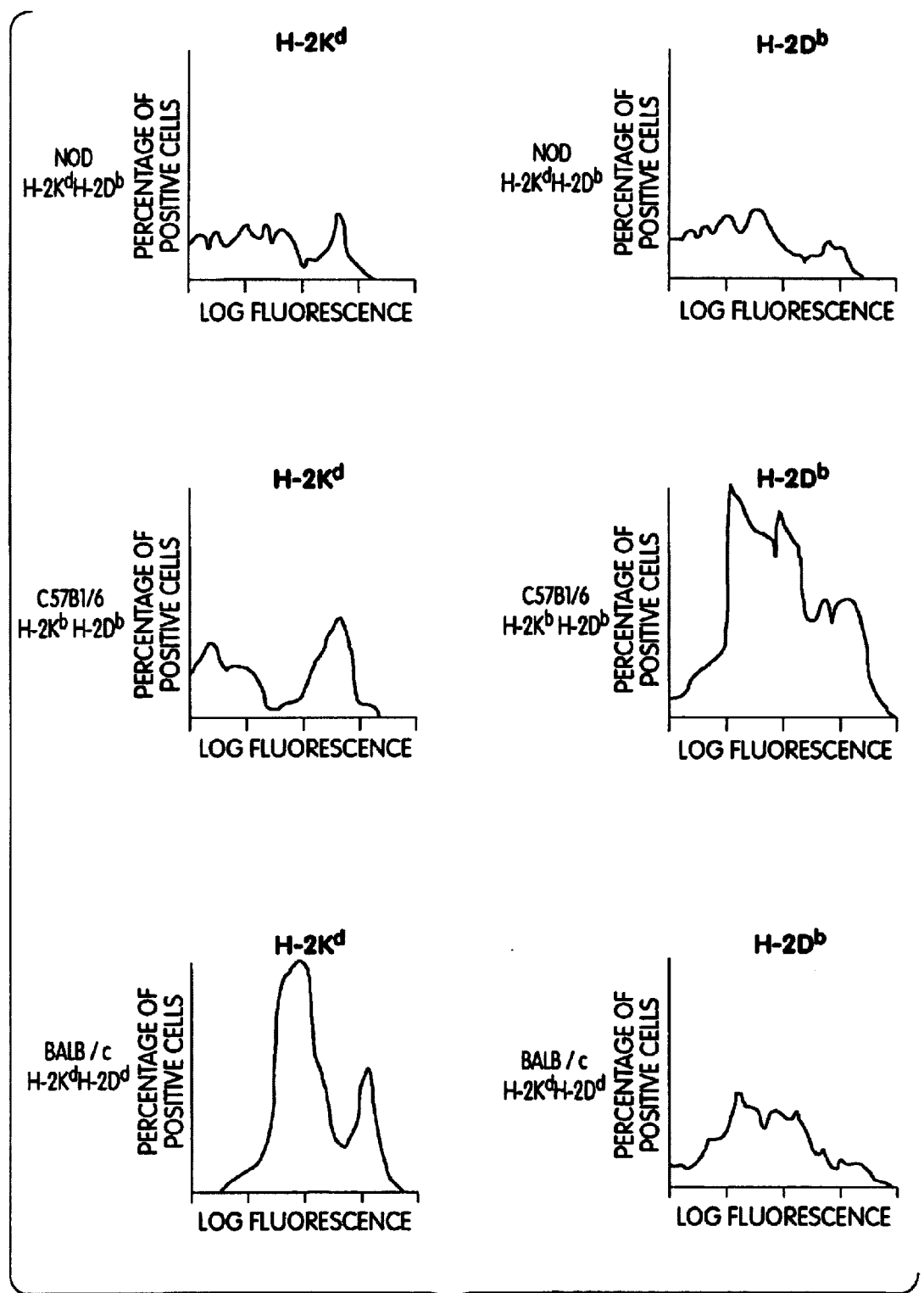
FIG. 2 is a set of graphs showing that NOD mice (a model for diabetes) have splenocytes markedly reduced in expression of HLA class I antigen.

The NOD mouse represents a well-characterized model for type I diabetes with a similar production of autoantibodies to insulin and/or islet cells weeks prior to frank hyperglycemia, as well as chronic lymphocytic infiltrates surrounding the islets prior to islet destruction. The HLA class I haplotype of the NOD mouse (H-2 loci) is H-2$K^d$ and H-2$D^b$. "Prediabetic" NOD splenocytes were analyzed by flow cytometry. Splenocytes were tested 6 and 20 weeks prior to frank hyperglycemia. Referring to FIG. 2, in ten NOD mice, 6+/−2.3% of the splenocytes bound to the H-2$K^d$ monoclonal antibody clone (31-3-45) compared to 88+/−15.8% positive splenocyte from positive control BALB/c mice. The mean antigen density for H-2$K^d$ was also significantly reduced for the NOD splenocytes compared to BALB/c splenocytes (p=0.001). A similar reduction in H-2$D^b$ expression on NOD splenocytes was also present. Using monoclonal antibody H141-31 directed to H-2$D^b$, 52+/−15% of NOD splenocytes were positive compared to 94+/−5.6% positive splenocytes from C57BL/6 mice (H-2$^b$) (n=10). H-2$^d$ haplotype BALB/c mice (n=10) were 38+/−7.8% positive with this H-2$D^b$ directed antibody, demonstrating that the NOD splenocytes were also severely reduced in the expression of this HLA class I antigen. Therefore, in both the human as well as the mouse, decreased HLA class I expression was observed on splenocytes in the NOD mouse and peripheral blood lymphocytes from diabetic humans.

Decreased HLA Class I Expressions in Other Autoimmune Diseases

The procedure described above, employing an HLA class I-specific monoclonal antibody, was carried out on peripheral blood lymphocytes from patients suffering from the following autoimmune diseases: Sjogren's syndrome; rheumatoid arthritis; type I polyendocrine failure; multiple sclerosis; SLE; hypothyroidism; Hashimoto's disease; and Graves' disease. In every instance there was decreased class I expression for lymphocytes obtained from patients with autoimmune disease in contrast to the normal MHC class I expression in non-autoimmune type II diabetic patients.

Artificial Interruption of HLA class I Expression in vivo is Sufficient for Autoimmune Type I Diabetes The following experiments were then carried out to determine whether defective HLA class I expression itself can lead to type I diabetes.

Mice homozygous for a $\beta_2$-micoglobulin deficiency do not express any detectable $\beta_2$ microglobulin and lack almost completely H-2K and partial H-2D major histocompatibility antigens on their cell surfaces. Ten mice over a year of age were checked for hyperglycemia, as well as body weight. All ten homozygous deficient mice greater than 1½ years of age were hyperglycemic as well as having a significant decrease in body weight compared to normal littermates of the same age (Table 1).

TABLE 1

Blood Sugar and Body Weight of HLA class I Deficient Mice Due to Lack of $B_2$-Microglobutin Genotype of Progeny

| | −/− | | +/− | |
|---|---|---|---|---|
| | BS (mg %) | Wt (gms) | BS (mg %) | Wt (gms) |
| | 239 | 22 | 92 | 37 |
| | 410 | 18 | 81 | 42 |
| | 333 | 16 | 76 | 31 |
| | 375 | 24 | 65 | 31 |
| | 396 | 27 | 62 | 35 |
| | 401 | 18 | 71 | 41 |
| | 339 | 21 | 80 | 32 |
| | 368 | 21 | 82 | 38 |
| | 347 | 26 | 77 | 37 |
| | 397 | 26 | 79 | 49 |
| Mean +/− S.D. | 360 +/− 50 | 21.9 +/− 3.8 | 79 +/− 8.73 | 37.3 +/− 5.6 |

(+/+ mice were not diabetic and had normal blood sugar and body weight)

Figure 3:
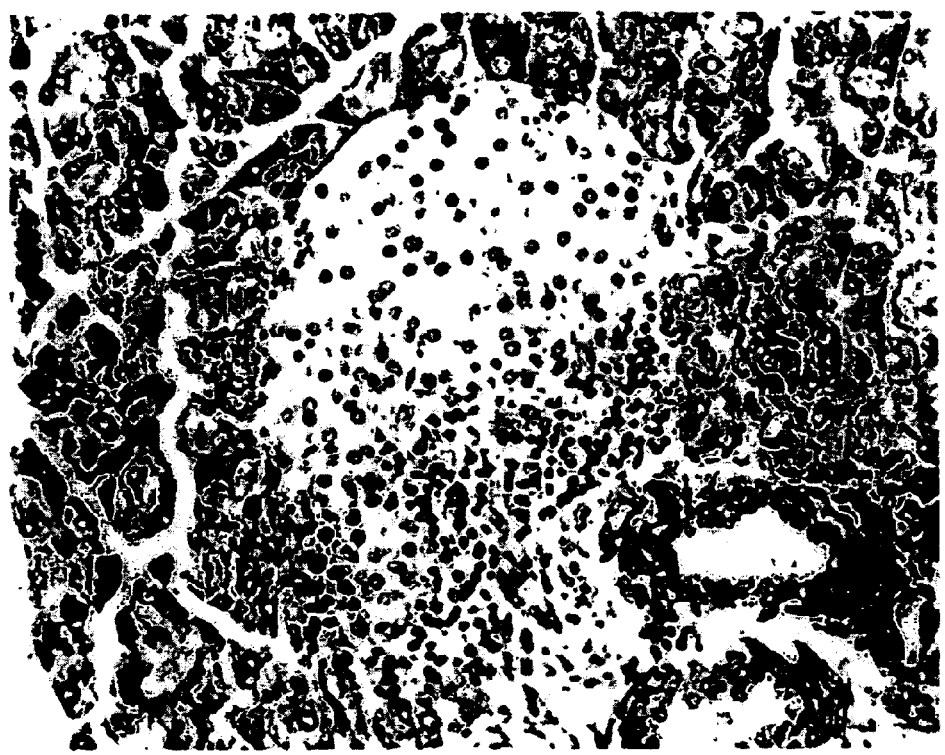
FIG. 3 is a photomicrograph of an islet from a $\beta_2$ microglobulin deficient mouse showing lymphocyte infiltration.

Histology was carried out on an islet cell of one of the mice homozygous for $\beta_2$ microglobulin deficiency, using hemotoxylin and eosin staining. FIG. 3 shows that the islet is surrounded with CD4+ lymphocytic infiltrates, as is typical of diabetic mice and humans. At the time of autopsy this mouse had an elevated blood sugar of 345 mg % and the few remaining islets were obscured by lymphocyte foci.

A test of the serum from a diabetic mouse revealed lymphocyte infiltration, providing further evidence for the autoimmune mechanism of this disease. Furthermore, since these homologous recombinant mice lack CD8 cells, this new model of autoimmunity suggests that islet destruction can be mediated without CD8 cells, thus suggesting a central and possibly exclusive role of CD4 or natural killer cell mediated islet attack. Although it appears that the onset of elevated blood sugars occurs after a year of age, a time point later than the hyperglycemia in the NOD mouse, the data clearly establishes the functional importance of HLA class I in the establishment of tolerance to self; moreover, the presence of a global defect in the presentation of self peptides on HLA class I is sufficient for the manifestations of a very focal form of clinically detectable autoimmunity, type I diabetes.

Decreased HLA Class I is Associated with in vitro Cytotoxicity to Self: a Lesson from Discordant Type I Diabetic Twins The following experiments were carried out to determine whether the reduced HLA class I molecules expressed on diabetic cells were phenotypically normal or impaired functionally in the presentation of endogenous antigens. It has previously been noted that macrophages and B-cells from a non-diabetic identical twin, when cultured with T-cells from the syngeneic diabetic twin, demonstrated augmented proliferation compared to the same incubation carried out with autologous components from either donor (i.e., an autologous mixed lymphocyte reaction-AMLR). In contrast, it was previously shown that the non-T-cells of the diabetic twin elicited less stimulation of the non-diabetic twin T-cells than does the autologous non-diabetic antigen presenting cells. It had also been shown that diabetic twin T-cell proliferation to HLA identical non-diabetic twin stimulators substantially exceeds the suppressed diabetic AMLR and also exceeds slightly control T-cell proliferation to self.

An explanation for these observations which is consistent with the discovery of the role of HLA class I in autoimmunity is that the somewhat hyper-responsive but "syngeneic" mixed lymphocyte reaction observed with non-diabetic antigen presenting cells and diabetic T-cells really represented an attenuated alloantigen response as in the mixed lymphocyte reaction (MLR) occurring because proper presentation of previously unrecognized endogenous peptides is provided by HLA class I on the non-diabetic stimulators. The diabetic twin T-cells would, therefore, recognize the non-diabetic twin peptides, now properly presented, as foreign due to the lack of previous exposure and tolerance induction.

A characteristic outcome of the MLR, not observed in an AMLR, is the generation of cytotoxic effector cells. To determine whether the syngenic MLR between non-diabetic antigen presenting cells and diabetic T-cells generated cytotoxic effectors, the following assay was performed. An AMLR with interchanges in stimulator cells was set-up between diabetic discordant twin pairs. A representative assay is shown in Table 2. After seven days of AMLR proliferation, the responding T-cells were harvested and used as possible autoreactive T-cells against chromium labelled self and twin targets in secondary cytotoxic T-lymphocyte assays. The data in Table 2 shows that diabetic twin T-cells demonstrated excessive proliferation of AMLR to non-diabetic twin stimulators lysed "syngeneic" twin targets but not self targets. As predicted, diabetic twin T-cells failed to generate autotoxicity to diabetic targets and autologous stimulated non-diabetic twin T-cells failed to lyse self. These results suggested that the previously observed excessive diabetic twin T-cell proliferation from co-culture with irradiated non-diabetic twin stimulators was secondary to the presentation of previously unrecognized self peptides. Most significantly, the autologous CTL production could be blocked by concealment of target HLA class I with a polyclonal HLA class I antibody, suggesting that the diabetic twin T-cell killing was directed toward the HLA class I epitope. In contrast, control CTL assays were not significantly blocked with this polyclonal antibody. These data suggest that autoreactivity to self antigens was present in diabetic twin T-cells, and could be unveiled in the context of correctly presented self peptides on HLA class I positive autologous cells.

TABLE 2

| | | AMLR ASSAY | | PERCENT SPECIFIC Cr RELEASE FROM TARGETS | | | | |
|---|---|---|---|---|---|---|---|---|
| | | | | | EFFECTOR TO TARGET CELL RATIO | | | |
| | | RESPONDERS T-Cells | STIMULATOR Non-T-Cells | TARGETS | 1:1 | 3:1 | 10:1 | 40:1 |
| A. | | Diabetic Twin | Diabetic Twin | Diabetic Twin | 1.3 +/ 0.4 | 0.9 +/− 0.4 | 4.5 +/− 0.3 | 5.4 +/− 0.2 |
| | | Non-diabetic Twin | Non-diabetic Twin | Non-diabetic Twin | 2.1 +/− 0.5 | 2.1 +/− 0.4 | 2.5 +/− 3.1 | 4.8 +/− 0.2 |
| | | Diabetic Twin | Non-diabetic Twin | Non-diabetic Twin | 16.2 +/− 1.9 | 20.1 +/− 1.5 | 40.0 +/− 2.0 | 59.0 +/− 6.2 |
| | | Non-diabetic Twin | Diabetic Twin | Non-diabetic Twin | 1.0 +/− 0.6 | .9 +/− 0.1 | 2.5 +/− 0.1 | 0.2 +/− 0.6 |

TABLE 2-continued

| AMLR ASSAY | | | PERCENT SPECIFIC Cr RELEASE FROM TARGETS | | | |
|---|---|---|---|---|---|---|
| | | | EFFECTOR TO TARGET CELL RATIO | | | |
| RESPONDERS T-Cells | STIMULATOR Non-T-Cells | TARGETS | 1:1 | 3:1 | 10:1 | 40:1 |
| | | | TREATMENT OF TARGET CELLS WITH HLA CLASS I ANTIBODY | | | |
| B. Diabetic Twin | Non-diabetic Twin | Diabetic Twin | 1.3 +/− 0.1 | 2.9 +/− 0.6 | 4.2 +/− 1.7 | 17.1 +/− 1.2 |

Diabetic and non-diabetic twin T-cells were stimulated for seven days at a 1:1 ratio with syagenoic stimulated non-T-cells from self or identical twins as previously described (#978). At day 7, the responding T-cells of the AMLR were harvested over Mcoil and the CTL assay performed. Target lymphocytes represented from lymphocytes from the donors which were thawed 24 hours prior to the assay. Targets were labelled with $Me_2 CrO_4$ at a concentration of 50–150 $\mu$ Cl of $^{51}Cr$ for $1 \times 10^6$ cells at 37° C. for one hour on a slow shaking platform. Target cells were washed gently two times prior to coculture with syagenoic stimulated T-cells for two hours at 37° C. at the above ratios. One hundred lambdas of the culture supernatant were harvested and counted in a gamma counter at the end of the assay. The above experiment was performed with triplicates. For part B, target cells were treated with a 1:100 dilution of sterile polyclonal mouse anti-human HLA class I serum (#978) for 30 minutes at room temperature, wash, and added to the culture plate for the cytotoxicity assay.

Defective T-cell Development in Diabetes is Secondary to Altered HLA Class I Expression and Presentation of Endogenous Peptides There has previously been described in diabetic humans a T-cell developmental defect with diabetic lymphoid cells expressing a disproportional increase in the numbers of lymphocytes expressing the low mean antigen density of many surface markers such as CD45, LFA-3, LFA-1, ICAM, CD2, etc., resulting in the lack of or diminution in the normal second peak of brightly fluorescent cells. In the human, the subpopulations of lymphoid cells in the dull peak have commonly been referred to as naive cells or suppressor inducer cells in contrast to the brightly fluorescent cells referred to as memory cells or helper-inducer cells. More recently, it has become clear that the increased dull to bright cells in diabetics is not only predictive of disease rate but secondary to a block in the normal transition from naive to memory T-cells with autologous development.

Figure 4A:
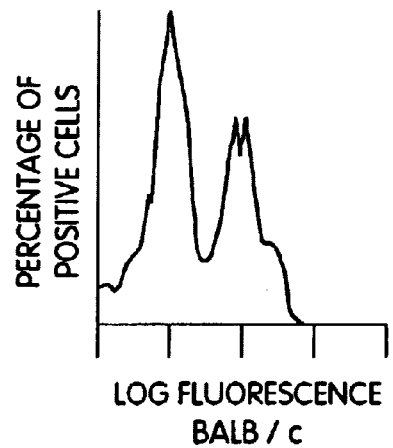
FIG. 4(A–C) is a set of FACS-generated graphs showing reactivity of normal and diabetic mouse lymphocytes with antibodies to isoforms of CD45.
Figure 4B:
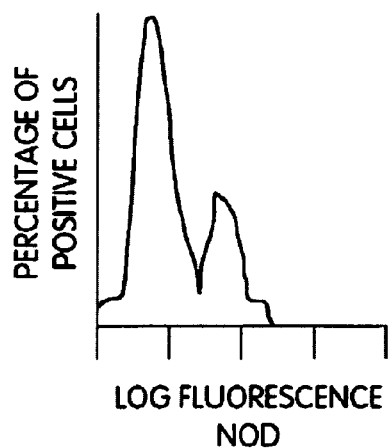
Figure 4C:
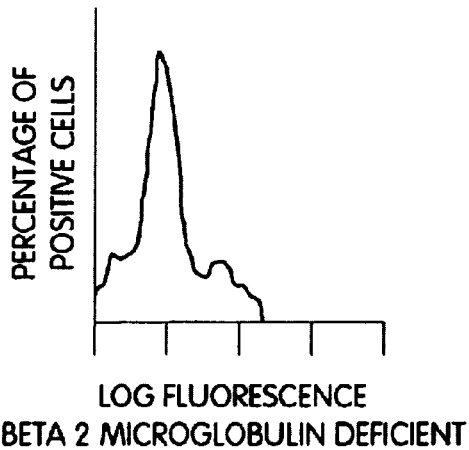

Murine monoclonal antibodies recognizing different CD45 isoforms have recently defined the mouse leukocyte common antigen. Antibody CD45R-1 (YCD45R-1) is specific for the high molecular weight isoforms of CD45, including exons A and B but excluding exon C. Normal BALB/c peripheral blood lymphocytes from mice stained with CD45R-1 demonstrate heterogeneity in expression, demonstrating the expected bimodal distribution in fluorescent intensity with dull and bright peaks (FIG. 4A). In marked contrast, NOD lymphocytes from the peripheral blood almost totally lack the high density CD45R. The $\beta_2$-microglobulin disruption mice, lacking HLA class I expression, exclusively express the low density population of CD45R, thus suggesting the central role of HLA class I presentation in lymphocyte maturation (FIG. 4C). Furthermore, analysis of the NOD mouse and HLA class I $\beta_2$-microglobulin deficient mouse revealed the lack of a high density peak for ICAM and two other CD45 antibodies on all peripheral blood lymphocytes, thus implicating the central developmental role of properly presented HLA class I as the possible ligand which drives development of peripheral lymphocytes.

Assay for mRNA Encoding an ATP-Dependent Transporter Protein

Mutations in the Tap-1 and Tap-2 genes have been found in a number of lymphoblastoid cell lines, such as murine RMA-S cells, human BM36.1, LCL721.174, and derivation T cell lines, all of which were selected for low cell surface expression of class I molecules. The surface expression of class I molecules on these mutant cell lines is not only reduced, especially as revealed with conformation-dependent anti-class I antibodies, but also unstable. Surface class I expression can be stabilized by low temperatures, which reduce the rate of turnover of surface class I molecules. The mutant cell lines also show delayed egress of class I molecules from the endoplasmic reticulum and are resistant to cytotoxic T cell (CTL) lysis (Cerundolo et al., Nature 345:449–452, 1990; Powis et al., Nature 354:528–531, 1991; Attaya et al., Nature 355:647–649, 1992; Townsend et al., Cell 62:285–295., 1990; Ljunggren et al., Nature 346:476–480, 1990; Shumacher et al., Cell 62:563–567, 1990).

Figure 5:
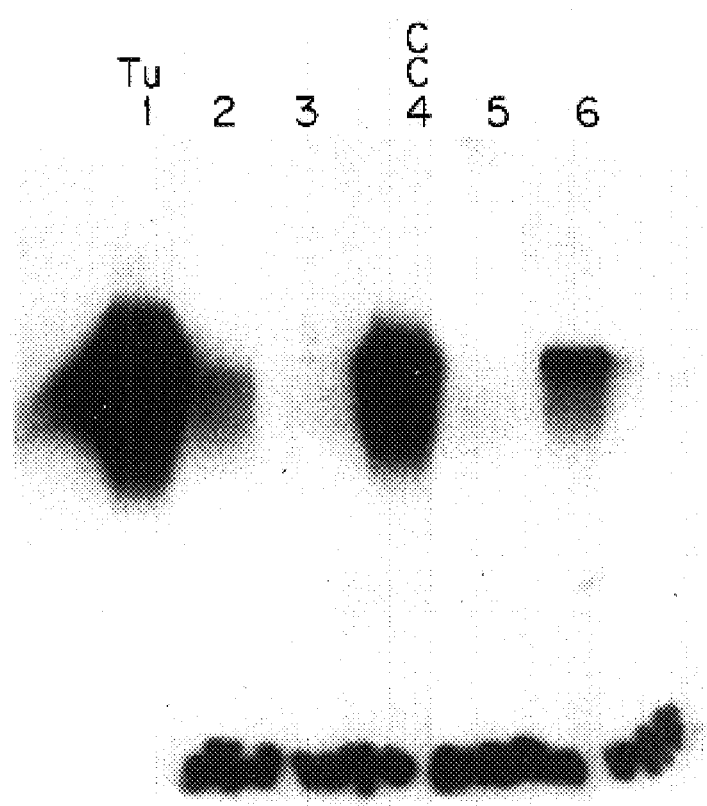
FIG. 5 is a Northern blot showing the lack of expression of the Tap-1 ATP-dependent transporter protein in diabetic lymphocytes compared to normal expression in a human control.

Referring to FIG. 5, a standard mRNA Northern blot assay was carried out for detecting the expression of one of the ATP-dependent transporter proteins, Tap-1, in a human tumor cell line, peripheral blood lymphocytes from long-term diabetics, and a normal control. A large amount of mRNA was detected in the human tumor cell line (lane 1). There is a virtual lack of Tap-1 mRNA in peripheral blood lymphocytes from long-term diabetics (lanes 2, 3, 5, and 6). In lymphocytes from the normal control individual, Tap-1 mRNA was present (lane 4).

RFLP Analysis of the Tap-1 Gene

Figure 6:
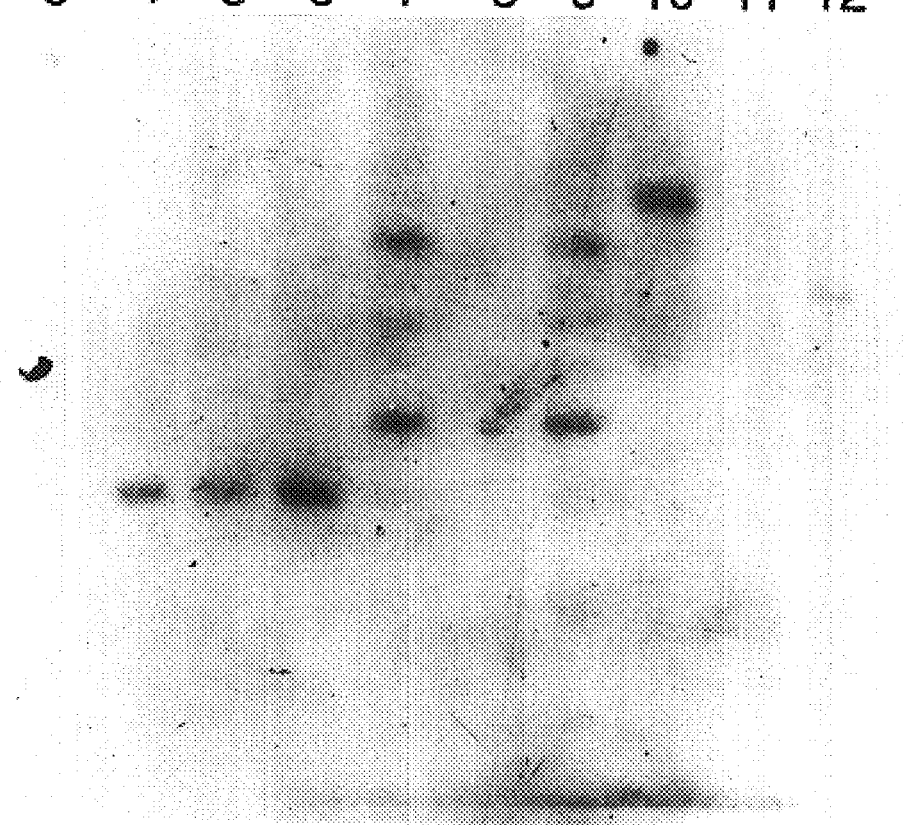
FIG. 6 is an RFLP Southern blot from the NOD mouse comparing DNA encoding an ATP-dependent transporter protein in lymphocytes from normal and diabetic patients. The figure clearly shows the large deletion in Tap-1 in the diabetic animal.
Figure 7:
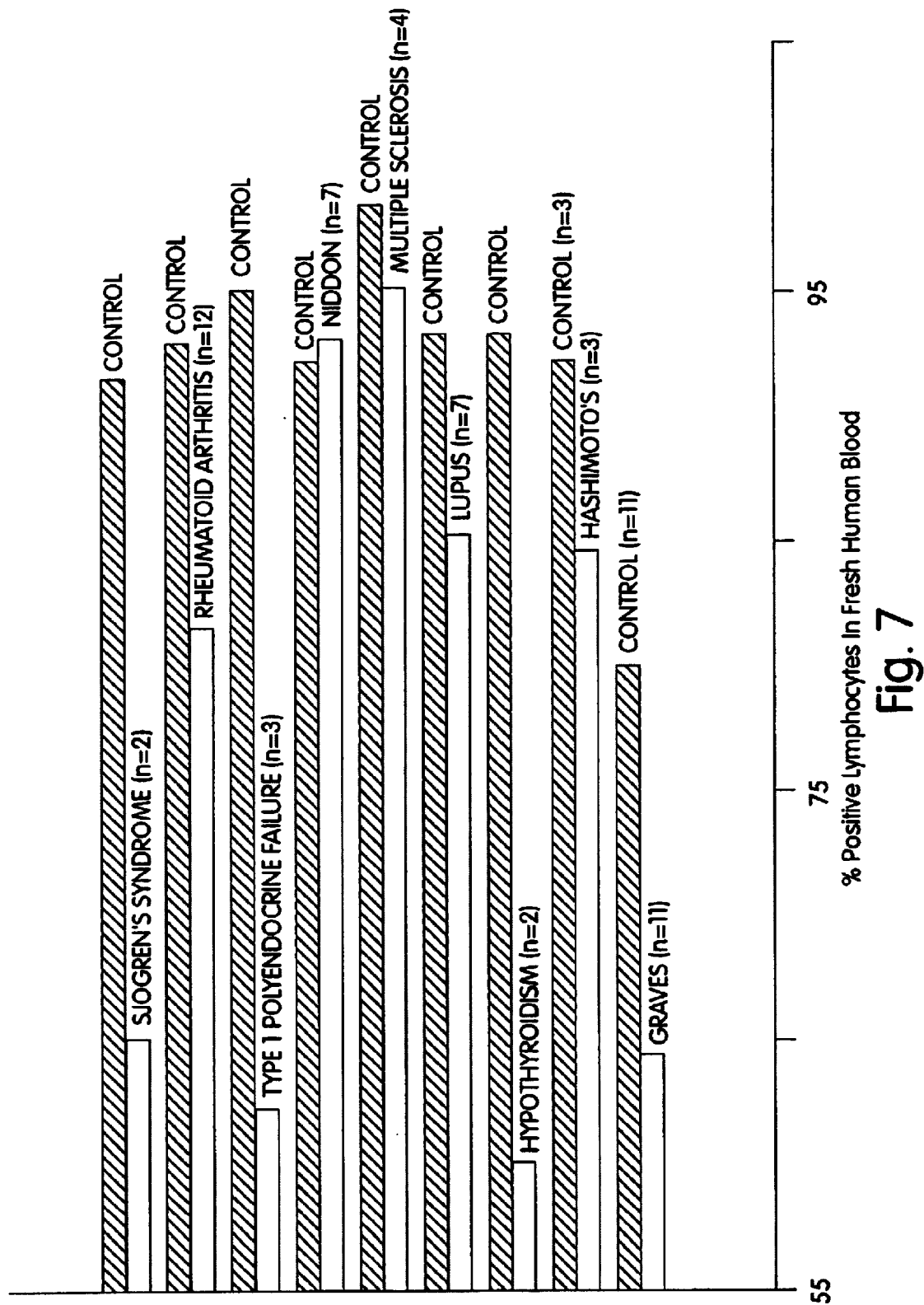
FIG. 7 is a bar graph showing decreased class I expression on cells taken from patients with various autoimmune diseases.
Figure 8A:
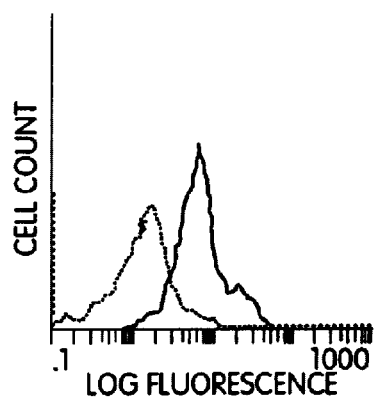
FIG. 8A is a FACS-generated graph showing surface $K^d$ class I expression on lymphocytes from NOD female mice (dashed line) compared to lymphocytes from control strains (solid line).
Figure 8B:
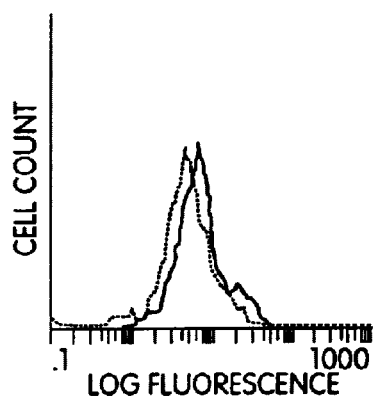
FIG. 8B is a FACS-generated graph showing surface $K^d$ class I expression on lymphocytes from NOD male mice (dashed line) compared to lymphocytes from control strains (solid line).
Figure 8C:
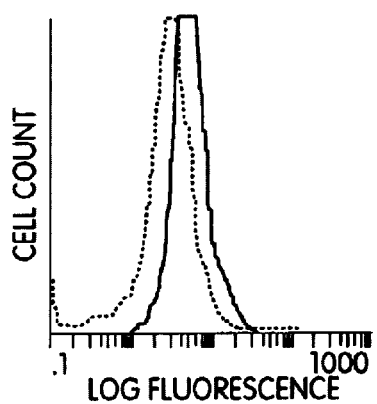
FIG. 8C is a FACS-generated graph showing surface $D^b$ class I expression on lymphocytes from NOD female mice (dashed line) compared to lymphocytes from control strains (solid line).
Figure 8D:
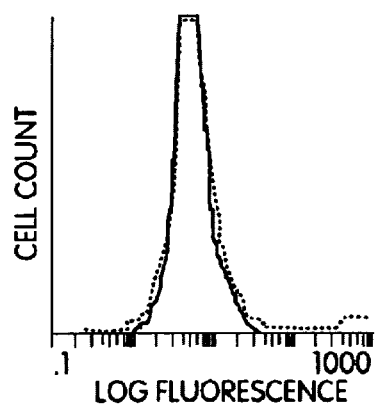
FIG. 8D is a FACS-generated graph showing surface $D^b$ class I expression on lymphocytes from NOD male mice (dashed line) compared to lymphocytes from control strains (solid line).

Referring to FIG. 6, RFLP analysis was carried out on NOD mouse DNA, and the results compared to BALB/c and C57 BL/6 control DNA, using Tap-1 DNA as a probe. DNA from spenocytes was prepared from NOD ($H-2K^d$ $I-A^d$), BALB/c ($H-2^d$) and C57BL/6 ($H-2^b$) mice and cut with a variety of enzymes followed by loading 5 $\mu$g of DNA per lane onto an agarose gel. A southern transfer was performed and the gene screen plus filter probed with Tap-1. DNA was run in Lane 1, 2, 3, 4, 5, 6, 7 (Lane 8 DNA improperly ran in the agarose gel and remained in the slot at the top of the gel.) Lanes 1, 4, and 7 represent BALB/c; Lanes 2 and 5, represent C57BL/6; and lanes 3, 6 and 9 represent NOD. The photo shows that the same probed bands could be visualized with BstEII or BamHI in Lanes 1, 2, 3 or 4, 6, 7. Lane 9 demonstrates the large deletion in the ATP-dependent transporter of the NOD with a significant decrease in probe band size in Lane 9 for the NOD DNA cut with XbaI compared to the BALB/c DNA on lane 7.

Correlation of Tap-1 Mutation with Faulty Antigen Presentation by Class I Molecules To investigate whether the low class I expression on antigen presenting cells (APCs) of diabetes-prone female NOD mice is associated with faulty loading of the class I molecules with endogenous peptides, NOD lymphocytes were examined for the well-characterized functional defects in class I assembly and antigen presentation associated with altered Tap-1 function.

Figure 9:
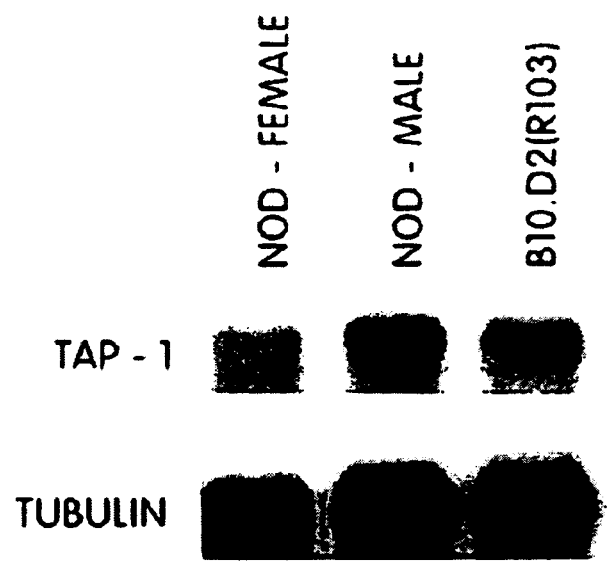
FIG. 9 is a Northern blot analysis of Tap-1 mRNA in NOD females and NOD males. mRNA preparations were analyzed by sequential hybridization of Northern blots with $^{32}P$-labeled Tap-1 (B5) and actin cDNAs.

Similar to many autoimmune diseases in humans, diabetes in NOD mice develops predominantly in females. In the colony used for these experiments, less than 3% of males develop hyperglycemia of 6 months of age, compared to 86% of females. Referring to Table 3 and FIG. 8, spleen cells isolated from NOD ($K^dD^b$), C57BL/6 ($K^bD^b$) and BALB/c ($K^dD^d$) mice between 8 and 11 weeks of age were incubated with fluorescein conjugated anti-$K^d$ antibody (#31-3-45) or fluorescein conjugated anti-$D^b$ antibody (H141-31) (both antibodies from Cedar Lanes, Westbury, N.Y.) and subjected to FACS analysis. The FACS analysis gate was set for either monocytes-macrophages or lymphocytes by size on forward light scatter versus log fluorescence. The monocyte-macrophage peak was verified by simultaneous use of a macrophage-specific antibody, and the lymphocyte peak was verified with antibodies to CD4 and CD8. Negative controls were stained with mouse immunoglobulin and the percentage positive cells was always less than 5%. The data show that all subpopulations of lymphocytes from female NOD mice that progress to hyperglycemia exhibit a reduced surface density (fluorescence) of class I molecules for both alleles of the class I genes $K^d$ and $D^b$, as revealed by fluorescence-activated cell sorting (FACS) analysis (FIG. 8, Table 3). Both lymphocytes and monocytes isolated from the spleen of male NOD mice showed levels of class I antigens indistinguishable from matched control mice (FIG. 8, Table 3). In addition, lymphocytes from male NOD mice with normal H-2$K^d$ or H-2$D^b$ expression also showed normal concentrations of Tap-1 mRNA (FIG. 9). Therefore, similar to the small number of female NOD mice that remain normoglycemic and have normal concentrations of Tap-1 mRNA and surface class I expression in lymphocytes, and vast majority of male NOD mice show normal surface expression of the $K^d$ and $D^b$ class I genes and normal constitutive Tap-1 mRNA abundance in lymphocytes.

TABLE 3

Surface density of class I molecules on lymphcytes and macrophages from NOD females and males and control mice.

| | Mean Fluorescence of class I | |
| --- | --- | --- |
| | Lymphocytes | Macrophages |
| H-2$K^d$ | | |
| NOD females | 3.0 +/− .74 | 17 +/− 9.2 |
| BALB/c females | 5.0 +/− 1.7 | 33 +/− 15 |
| | p < .000 | p < .000 |
| | (n = 21) | (n = 21) |
| NOD males | 4.8 +/− 1.5 | 37 +/− 22 |
| BALB/c males | 5.4 +/− 1.6 | 34 +/− 15 |
| | p = .14 | p = .50 |
| | (n = 11) | (n = 11) |
| H-2$D^b$ | | |
| NOD females | 5.2 +/− 2.7 | 20 +/− 8.2 |
| C57BL/6 females | 7.9 +/− 2.1 | 32 +/− 7.9 |
| | p = .005 | p = .012 |
| | (n = 11) | (n = 10) |

TABLE 3-continued

Surface density of class I molecules on lymphcytes and macrophages from NOD females and males and control mice.

| | Mean Fluorescence of class I | |
| --- | --- | --- |
| | Lymphocytes | Macrophages |
| NOD males | 7.3 +/− 5.5 | 36 +/− 23 |
| C57BL/6 males | 8.0 +/− 3.3 | 32 +/− 14 |
| | p = .52 | p = .35 |
| | (n = 10) | (n = 19) |

The NOD samples were compared to simultaneously prepared control samples to prevent analysis-day-effect errors. The number of paired samples is indicated by n, and the data were analyzed by a paired t test.

Class I Expression can be Stabilized in Transporter-mutant RMA-S Cells by Incubation at Reduced Temperatures.

Splenocytes from female NOD mice were incubated at a density of $10^6$ cells/ml in RPMI-1640 containing 10% fetal bovine serum (FBS) supplemented with antibiotics under 5% $CO_2$ at reduced temperatures in an attempt to reduce the suspected accelerated rate of turnover of the empty $K^d$ or $D^b$ molecules. Female NOD mouse lymphocytes cultured at 28° C. for greater than 18 hours demonstrated increased class I expression as revealed by staining with an anti-$K^d$ antibody and FACS analysis (FIG. 10A). In addition, culture of NOD female splenocytes at temperatures of 25, 28, and 37° C. for 24 hours demonstrated that normalization of $K^d$ (FIG. 10B) and $D^b$ expression occurred on macrophages only at 25 and 28° C.

Enhanced Stability of Class I Expression on the Surface of Transporter-mutant Cell Lines can also be Achieved by Treatment of Cells with Synthetic Peptides.

Female NOD splenocytes were cultured with a $K^d$ allele-specific peptide in an attempt to load the empty peptide groove of this class I molecule. The peptide corresponding to amino acids 147 to 155 of the influenza virus A/PR/8/34 nucleoprotein is presented in the H-2$K^d$ groove to H-2 restricted CTLS. Splenocytes from female NOD mice and controls were cultured in serum-containing medium at 37° C. with or without $K^d$-specific peptide for 5 hours, and then analyzed by FACS with an anti-$K^d$ antibody. The $K^d$-specific peptide, Thr-Tyr-Gln-Arg-Thr-Arg-Ala-Leu-Val (SEQ ID NO:1), represents amino acids 147 to 155 from the influenza virus A/PR/8/34 nucleoprotein (Rotzschke et al., *Nature* 348:252–254, 1990) and was synthesized by Chiron Mimotopes (Emeryville, Calif.). Incubation with the synthetic peptide at a concentration of 480 $\mu$M stabilized the surface expression of $K^d$ in female NOD mouse macrophages over the course of a 5-hour incubation at 37° C., but incubation of this peptide with control class I-identical B10.D2 (R103) splenocytes resulted in no change in mean fluorescence attributable to $K^d$ (FIG. 11a). Data are given in means +/− SEM for two female B10.D2 (R103) mice and two female NOD mice in a representative experiment, which was repeated five times with similar results. The restoration and stabilization of $K^d$ expression on female NOD splenocytes with allele-specific peptide was dose dependent with concentrations greater than 240 $\mu$M being optimal (FIG. 11B).

Intracellular Transport of Class I Molecules.

Transport of class I molecules from the endoplasmic reticulum to the Golgi can be estimated by the rate of sialylation of these molecules, which occurs in the Golgi and results in an increase in their molecular mass as revealed by SDS-polyacrylamide gel electrophoresis. In [$^{35}$S]-methionine pulse-chase experiments, splenocytes were incubated at 37° C. for 90 minutes in methionine-free medium and then labeled with [$^{35}$S]methionine (10 mCi/ml) for 15 to 20 min. The [$^{35}$S]methionine medium was removed and the cells were washed once and then resuspended in medium containing 16.7 mM unlabeled methionine. Cells (5×10$^6$ or 1×10$^7$) were subsequently harvested at various times, lysed with 0.5 to 1.0 ml of 1% Triton-X100 lysis buffer, and subjected to immunoprecipitation with a conformational-independent antibody to D$^b$ [clone 28-14-8S; American Type Culture Collection (ATCC), Bethesda, Md.]. Immunoprecipitates were analyzed by SDS-polyacrylamide gel electrophoresis on a 12% gel.

Immunoprecipitates from control antibody to the conformation-independent α3 region of D$^b$ revealed similar rates of class I glycan modification (FIG. 12). In contrast, female NOD splenocytes exhibited markedly reduced and delayed delivery of class I molecules into the trans-Golgi (FIG. 12), presumably indicative of failed assembly of the trimer complex of class I molecule, self peptide, and β$_2$-microglobulin in the endoplasmic reticulum. Similar results to those obtained with the anti-D$^b$ antibody were observed with a K$^d$-precipitating antibody for splenocytes from a B10.D2 (R103) female and a NOD female.

NOD Cells are not Susceptible to Restricted CTL Lysis.

Female NOD lymphocytes were tested for the ability to serve as targets for lysis by K$^d$- or D$^b$-restricted, influenza virus (A/JAP)-specific CTL clones or bulk CTLs. Alloreactive CTLs were generated as bulk CTL isolated from splenocytes by in vivo followed by in vitro priming of BALB/c (K$^d$, D$^d$), B10.A(2R), (K$^k$, D$^b$), D2.GD (K$^d$, D$^b$) or C57BL/6 (K$^b$D$^b$) mice with live influenza virus A2/Japan/305/57 (ATCC VR-100) (A/JAP). Mice were injected intraperitoneally with 0.3 ml of a virus stock solution (1 ml of stock solution contained q median tissue culture infections dose of 10$^6$ to 10$^{8.5}$ 0.2 ml) in phosphate-buffered saline. Two to three weeks later, the animals were injected with a further 0.15 ml of virus stock solution. Two days later, the animals were killed, and splenocytes were prepared (1×10$^6$ to 5×10$^6$ cells/ml) and cultured in RPMI containing 10% FBS and live virus stock solution at (20 ul/ml). After 5 to 6 days in culture, the splenocytes were centrifuged over Ficoll (Pharmacia) to obtain viable CTLs, which were resuspended in medium at the appropriate effector to target ratios for the cytotoxicity assay. Target lymphocytes were prepared from lipopolysaccharide (LPS)-stimulated splenocytes. Splenocytes harvested from female mice were cultured for 2 to 3 days in RPMI with 10% FBS, 50 μM 2-mercaptoethanol and LPS (40 μg/ml) (Difco, Grand Rapids, Mich.). Cells (10$^7$/ml) were then incubated with $^{51}$Cr (0.1 mCi/ml) at 37° C. for 1 hour. After three gentle washes, the $^{51}$Cr-labeled targets were then incubated with live virus (100 μl.ml) for 60 min at 37° C. The target cells were then plated at a concentration of 10$^5$ cells per well with the appropriate number of CTL effectors to generate the described effector to target ratios (Table 4).

Both D$^b$-restricted and K$^d$-restricted bulk CTLs showed negligible or no killing of virus-exposed NOD female targets (Table 4). Normal CTL lysis of class I-matched targets pulsed with live virus was observed for many different control strains. In addition, both the K$^d$-restricted CTL clone 14-1 and the D$^b$-restricted CTL clone 11-1 failed to lyse female NOD target lymphocytes. The resistance of female NOD lymphocytes to class I-restricted peptide-specific CTLs suggests that, similar to mutant RMA-S and LCLC 721.174 cells, peptide-loaded class I molecules are not present on the surface of these cells.

TABLE 4

Susceptibility of NOD and control strain target cells to class 1-restricted influcoza virus A/JAP -specific CTLs.

| | | | Specific Lysis (%) |||||
| | | | Effector: Bulk H-2D$^b$ CTLs from C57BL/6 |||||
| Target Cells | H-2 | Target | Exp 1 | Exp 2 | Exp 3 | Exp 4 | Exp 5 |
|---|---|---|---|---|---|---|---|
| NOD | D$^b$ | 10:1 | 0% | 0% | 0% | 0% | 12% |
| C57BL/6 | D$^b$ | 10:1 | 9% | 9% | 33% | 28% | 40% |
| B10.D2 (R103) | D$^b$ | 10:1 | 12% | 30% | 60% | 63% | 38% |

| | | | Specific Lysis (%) |||||
| | | | Effector: Bulk H-2K$^d$ CTLs from BALB/c |||||
| Target Cells | H-2 | Target | Exp 1 | Exp 2 | Exp 3 | Exp 4 | Exp 5 |
|---|---|---|---|---|---|---|---|
| NOD | K$^d$ | 10:1 | 0% | 0% | 0% | 32% | 0% |
| D2GD | K$^d$ | 10:1 | — | 15% | — | 40% | |
| B10.D2 (R103) | K$^d$ | 10:1 | 26% | — | 50% | — | 48% |
| BALB/c | K$^d$ | 10:1 | 9% | 24% | 48% | 72% | — |

| | | | Specific Lysis (%) ||||
| | | | Effector: Bulk H-2K$^d$ CTLs from B10.A (2B) ||||
| Target Cells | H-2 | Target | Exp 1 | Exp 2 | Exp 3 | Exp 4 |
|---|---|---|---|---|---|---|
| NOD | D$^b$ | 10:1 | 0% | 0% | 0% | 0% |
| | | 2:1 | 0% | 0% | 0% | 0% |
| B10.A (2R) | D$^b$ | 10:1 | 15% | 18% | 12% | 60% |
| | | 2:1 | 9% | 7% | 0% | 0% |
| C57BL/6 | D$^b$ | 10:1 | 100% | — | 36% | 32% |
| | | 2:1 | 58% | — | 0% | 25% |

| | | | Specific Lysis (%) ||||
| | | | Effector: CTL clone 14-1 against K$^d$ ||||
| Target Cells | H-2 | Target | Exp 1 | Exp 2 | Exp 3 | Exp 4 |
|---|---|---|---|---|---|---|
| NOD | K$^d$ | 5:1 | 0% | 0% | 0% | 0% |
| B10.D2 (R103) | K$^d$ | 5:1 | 25% | 33% | 50% | 33% |
| BALB/c | K$^d$ | 5:1 | 12% | 9% | 14% | 9% |

| | | | Specific Lysis (%) ||
| | | | Effector: CTL clone 11-1 against K$^d$ ||
| Target Cells | H-2 | Target | Exp 1 | Exp 2 |
|---|---|---|---|---|
| NOD | K$^d$ | 5:1 | 0% | 3% |
| D2GD | K$^d$ | 5:1 | 13% | 21% |
| BALB/c | K$^d$ | 5:1 | 17% | 37% |

The CTL preparations did not generate specific lysis on targets not incubated with virus; these control results are therefore not shown. CTL clones 14.1 and 11.1 are H-2K$^d$-restricted CTLs specific for hemagglutinin from A/JAP of the H2N2 subtype [#967]. All are expressed as percent specific lysis and data represents mean +/− SD. In each section of the table, n represents the number of individual experiments that generated the accompanying cytotoxicity data.

Class I Molecules Exported to the Cell Surface in NOD Cells Lack Peptide in their Antigen Binding Pocket.

Female NOD mouse lymphocytes were incubated at 28° C. for 24 hours and then used them as targets for K$^d$ or D$^b$ restricted influenza virus-specific CTLs. The phenotypic correction of class I expression on female NOD targets by low-temperature culture did not restore susceptibility to specific CTL lysis (Table 5). This result suggests that the increased class I expression on the surface of female NOD lymphocytes at 28° C. is attributable to empty class I molecules.

In contrast, the phenotypic correction of class I expression on female NOD lymphocytes achieved by incubation with class I-specific peptide did restore susceptibility to CTLs (Table 6). Neither the susceptibility of control BALB/c targets nor that of NOD male targets to CTL lysis was affected by prior incubation with $K^d$-specific peptide (Table 6).

TABLE 5

Effect of phenotypic correction of class I expression on NOD targets by low-temperature culture (28° C.) on the susceptibility to CTL lysis.

| Target Cells | Effector: Target | H-2 | Specific Lysis (%) | | | |
|---|---|---|---|---|---|---|
| | | | Exp 1 | Exp 2 | Exp 3 | Exp 4 |
| Bulk H-2D$^b$ and A/JAP virus specific CTLs from C57BL/6 or B10.A(2R) | | | | | | |
| NOD | 10:1 | D$^b$ | 0% | 0% | 0% | 0% |
| | 2:1 | D$^b$ | 0% | 0% | 0% | 0% |
| BALB/c | 10:1 | D$^b$ | 100% | 34% | —% | 51% |
| | 2:1 | D$^b$ | 24% | 18% | —% | 80% |
| B10.D2 (R103) | 10:1 | D$^b$ | 18% | — | 38% | 28% |
| | 2:1 | D$^b$ | 31% | — | 46% | 23% |
| Bulk H-2K$^d$ and A/JAP or A/PR virus specific CTLs from BALB/c | | | | | | |
| NOD | 10:1 | K$^d$ | 0% | 0% | 0% | |
| | 2:1 | K$^d$ | 0% | 0% | 0% | |
| BALB/c | 10:1 | K$^d$ | 52% | 34% | 98% | |
| | 2:1 | K$^d$ | 14% | 18% | 88% | |
| B10.D2 (R103) | 10:1 | K$^d$ | 24% | — | 38% | |
| | 2:1 | K$^d$ | 11% | — | 12% | |

Targets from female mice were calculated on day 2 after isolation at 28° C. for 14 to 20 hours, prior to $^{51}$Cr labeling and viral pulsing. Data for the D$^b$-restricted CTLs is derived from five separate cytotoxicity assays, except for the B10.A(2R) group, which represents three separate assays. Data for the K$^d$-restricted CTLs is derived from nine separate assays for the NOD and BALB/c groups, and three assays for the B10.D2(R103) group. Values represent means +/− SD.

TABLE 6

Effect of exogenous class I-specific peptide on susceptibility of female NOD target cells to CTL lysis.

| Target Strain | Sex | Exogenous Peptide | Live Virus | | Exp 1 | Exp 2 | Exp 3 | Exp 4 |
|---|---|---|---|---|---|---|---|---|
| NOD | F | − | + | 10:1 | 8% | 0% | 0% | 6% |
| | | − | + | 5:1 | 9% | 0% | 0% | 0% |
| NOD | F | + | − | 10:1 | 24% | 9% | 48% | 33% |
| | | + | − | 5:1 | 20% | 4% | 0% | 12% |
| NOD | M | − | + | 10:1 | — | — | 60% | 20% |
| | | − | + | 5:1 | — | — | 7% | 17% |
| NOD | M | + | − | 10:1 | — | — | 21% | 100% |
| | | + | − | 5:1 | — | — | 0% | 17% |
| BALB/c | F | − | + | 10:1 | 45% | 15% | 58% | 20% |
| | | − | + | 5:1 | 0% | 0% | 6% | 18% |
| BALB/c | F | + | − | 10:1 | 24% | 39% | 50% | 100% |
| | | + | − | 5:1 | 20% | 12% | 20% | 76% |

H-2K$^d$ target cells from male or female mice were incubated either with live A/PR virus or with synthetic A/PR viral peptide fragment Thr-Tyr-Gln-Arg-Thr-Arg-Ala-Leu-Val. Bulk K$^d$-restricted, A/PR virus-specific CTLs were prepared from BALB/c mice and showed no cytotoxicity against irrelevant virus infected targets, [C57BL/6 (H-2 D$^b$) or against relevant targets, (BALB/c) not exposed to virus represent five separateCTL assays. Alternatively the targets were incubated at this step with control media (no virus) or 5 ug/ml of the appropriate class I specific viral peptide fragment.

The ability of male NOD lymphocytes to serve as targets for $K^d$- or $D^b$-restricted specific for influenza virus was also investigated. The susceptibility to CTL-mediated lysis of NOD male targets was similar to that of haplotype-matched control targets (Table 7). Class I molecules on male NOD lymphocytes therefore appear to present the correct peptide epitope for CTL lysis with an efficiency comparable to control targets—as would be expected if Tap-1 functioned normally in these non-diabetes-prone mice. Two rare female NOD mice that consistently showed normal surface expression of class I molecules and, at the time of killing for these experiments, had normal Tap-1 and Tap-2 mRNA concentrations were also examined: one mouse supplied targets for $D^b$-restricted CTLs and the other provided targets for $K^d$-restricted CTLs. In both cases, the target cells were susceptible to CTL lysis (Table 7).

TABLE 7

Susceptibility of target cells from NOD females and males to CTL lysis.

| Effector Target | H-2 | Exp 1 | Exp 2 | Exp 3 |
|---|---|---|---|---|
| Bulk H-2D$^b$-restricted, virus-specific CTLs from A/JAP C57BL/6 | | | | |
| NOD males | 10:1 | D$^b$ | 39% | 32% | — |
| | 2:1 | | 36% | 25% | — |
| NOD females | 10:1 | D$^b$ | 0% | 0% | — |
| | 2:1 | | 0% | 0% | — |
| NOD female* | 10:1 | D$^b$ | — | — | 13% |
| | 2:1 | | — | — | 17% |
| C57BL/6 | 10:1 | D$^b$ | — | — | 38% |
| | 2:1 | | — | — | 40% |
| B10.D2(R103) | 10:1 | D$^b$ | 1% | 60% | 32% |
| | 2:1 | | 12% | 0% | 38% |
| Bulk H-2K$^d$-restricted A/PR virus-specific CTLs from BALB/c | | | | |
| NOD males | 10:1 | K$^d$ | 26% | 60% | — |
| | 2:1 | | 14% | 7% | — |
| NOD females | 10:1 | K$^d$ | 6% | 0% | — |
| | 2:1 | | 0.3% | 0% | — |
| NOD female* | 10:1 | K$^d$ | — | — | 32% |
| | 2:1 | | — | — | — |
| BALB/c | 10:1 | K$^d$ | 20% | 58% | 72% |
| | 2:1 | | 18% | 6% | — |

Data for the H-2D$^b$-restricted CTLs represent two separate experiments for NOD male targets, three experiments for C57BL/6 and B10.D2(R103) targets, and five separate experiments for NOD females. Data for the H-2K$^d$-restricted CTLs represent seven experiments for NOD female and BALB/c targets and three experiments for NOD males. In each case, the asterisk indicates two female NOD mice that showed normal class I expression.

In summary, diabetes-prone female NOD mice exhibit reduced cell surface expression of class I molecules, a reduced rate of transport from the endoplasmic reticulum to the Golgi, and a failure to present internally derived cytoplasmic antigen fragments to CTLs. However, surface class I expression can be stabilized by low temperatures, and the addition of exogenous peptides increases stability of class I expression on the cell surface as well as restores sensitivity to CTL lysis. In contrast, non-diabetes-prone NOD male mice show normal class I expression at the cell surface, normal egress of class I molecules from the endoplasmic reticulum, normal Tap-1 mRNA abundance, and normal susceptibility to class I-restricted peptide-specific CTLs. The simplest interpretation of these data is that the decreased expression of Tap-1 in female NOD mice hampers presentation of self peptides.

The above data demonstrate the central role of HLA class I expression and disease course in autoimmunity. For example, independent of genotype only the subset of NOD mice with decreased HLA class I expression develops diabetes. In identical twins discordant for IDDM, only identical twins with IDDM have reduced HlA class I expression on peripheral blood lymphocytes; the nondiabetic twins have normal or near normal HLA class I expression. From these results it appears that proper HLA class I antigen presentation may be a pathway for self-tolerance which, if altered, regardless of genotype, can lead to autoimmune disease.

Therapy

As discussed above, the discoveries of the invention make possible therapies for autoimmune diseases, as well as therapies in which tolerance to a particular protein antigen is desired, e.g., in prevention of allograft rejection. Some of these therapies will now be discussed in more detail.

Gene Therapy

Where a patient suffers from or has the propensity to develop an autoimmune disease such as type I diabetes because of a defect in, or deletion of, one of the proteins involved in processing or transport of self antigens for complexation with class I, or processing of the complex (MHC class I; endogenous peptide and beta 2 microglobulin) successfully to the cell surface, or a defect or deletion in a class I gene itself, one mode of therapy involves transfecting cells with a missing or defective gene and reintroducing those cells into the patient. The functional protein in those cells will process or transport the endogenous, cytosolic proteins into the endoplasmic reticulum for complexation with HLA class I for presentation on the cell surface, an event which will induce self-tolerance and inhibit the development of the autoimmune disease. This therapy ideally is carried out prior to advanced stages of the disease, e.g., preferably, in the case of type I diabetes, in patients who are at high risk because of anti-insulin and anti-islet antibodies, but who have not yet undergone destruction of the islet cells.

The first step is to identify the missing or defective gene, according to one of the methods described above. Once that identification has been made, cells which are capable of presenting antigens complexed with class I are transfected with the missing or defective gene, by standard eukaryotic transfection techniques. The transfected cells are preferably the patient's own cells, and preferably are lymphoid cells such as B cells or macrophages, which are known to be antigen presenting cells. The B-cells can be transiently tranfected, so as to avoid production of a permanent cell line; in this instance, introduction of the autologous transfected B-cells will need to be carried out periodically, e.g., every few months, as the B-cells die out. Alternatively, an immortalized cell line can be made from the patients B-cells, e.g., by infection with EBV. The cells could be engineered so as to make them susceptible to an antibiotic, so that after they have induced tolerance in the patient, the patient can be administered the antibiotic to kill the cells and prevent them from forming neoplasms.

Lymphocytes from other individuals can also be used to induce tolerance to common self-antigens. Preferably, the lymphocytes are taken from an individual who has been HLA-matched with the patient using standard matching techniques. The individual providing the lymphocytes must be one whose HLA class I antigen presentation is normal, so that the antigens not presented by the patient because of the class I presentation defect are presented on the donor cells. The donor cells can be provided as a purified fraction of serum, or in whole blood. If the lymphocyte fraction is used, a monthly infusion on the order of $1\times10^8$ cells might be sufficient to induce self-tolerance and prevent development of diabetes or another autoimmune disease. Furthermore, these cells can be irradiated prior to infusion to prevent graft versus host disease or the transmission of any infectious disease because dead cells still present already processed antigens in the HLA class I binding cleft.

Examples of the manner in which permanent and transient B cell transfections will be carried out follow.

Permanent Transfection with a Multi-Drug Resistant Transporter

The first step is to isolate B cells or lymphocytes from a patient predisposed to or suffering from an autoimmune disease because of a class I presentation defect caused by a missing or defective class I gene, proteosome gene, or ATP-dependent transporter gene (e.g., Tap-1 or Tap-2). The mRNA from the patient is analyzed to identify the defective or missing gene. The patient's isolated B cells are immortalized by standard procedures using EBV, producing a tumor line based on the patient's cells. Following establishment and immortalization of the cell line, the cells are made sensitive to a "suicide" antibiotic by transfection, using standard techniques, with a gene conferring antibiotic sensitivity.

Transfection of the B cell line to allow expression of the missing or defective transporter protein can then be carried out as follows. Transfection will be performed using a cDNA molecule encoding the missing or defective protein, which cDNA will include the 72 base pairs located upstream from the translation initiation codon, which terminates two base pairs downstream from the polyadenylation site. The cDNA will be inserted into a vector such as pcDNA I/NEO (In Vitrogen) under the transcriptional control of a cytomegalovirus promoter and enhancer. Transformants will be selected for resistance to neomycin (G418). Transformants will be examined at three to four weeks following transfection to identify, by flow cytometry, those expressing on their surfaces HLA class I antigens; this can be accomplished, e.g., using a monoclonal antibody such as W6/32, which recognizes all HLA class I of humans.

Other expression vectors of course can be used as well, e.g., RSV.5 (DPT), in which CDNA transcription is driven by the ROUS sarcomavirus 5' long-terminal repeat. In this vector, an RSV.5 (DPT) guanine phosphoribosyl transferase gene confers resistance to mycophenolic acid.

Following successful transfection and screening for HLA class I antigen expression, sublines optimally expressing such antigens will be established for reinfusion into the patient. Following infusion and determination that tolerance to self has been achieved, the antibiotic to which the cells have been made sensitive is administered to the patient to kill the cells.

The transfection step mentioned above can be carried out using any standard technique. Generally, in either of the vectors mentioned above, insertion of the cDNA encoding the transporter protein can employ flanking polylinker restriction sites such as HindIII and NotI and XbaI. Transfection can be carried out using electroporation apparatus (BIORAD) at 1250 volts, 3 capacitor banks, minimalized time, and maximal fall time. Cells are cultured at about $5\times10^5$ cells per ml for at least two days prior to electroporation. Cells at a concentration of $5\times10^6$ are then suspended in 0.5 ml of culture media (RPM1 1640/15% fetal calf serum) in electroporation cuvettes placed in an ice water bath. After electroporation, cells are maintained at room temperature for ten minutes, resuspended in fresh culture media, and distributed into multi-well plates. The amount of DNA per cuvette will be between 3 and 20 micrograms.

Selection for correctly transfected cell lines will be started on Day 5 after electroporation, using G418 (Gibco) for pcDNA 1/NEO and mycophenolic acid (Sigma) immediately containing Xanthine (10 micrograms per ml) for RSV.5 (DPT). After two weeks of selection, drug resistant cell populations proliferating in many wells will be examined individually. Analysis of the transfectant cell populations by flow cytometry will begin five weeks after electroporation.

Cells will be maintained after that point at 3 to $8\times10^5$ cells per ml for two to three days and stained by indirect fluorescence according to conventional methods. Cell lines expressing high amounts of HLA class I will be subcloned and selected cell populations will be sampled for reinfusion into the patient.

Patients will be immunized weekly with $1\times10^6$ to $1\times10^8$ cells per dose intravenously; re-establishment of tolerance to self will be monitored by sampling T-cells from the recipient for proper T-cell development, i.e. re-establishment of the high peak of CD45 or ICAM or other memory cell markers, as well as for the lack of cytotoxic T-cells to autologous antigen presenting cells that have not yet been permanently transfected.

Transient Transfection

An alternative procedure for re-establishment of tolerance to self will be to perform transient transfections on freshly isolated antigen presenting cells such as B cells. As previously outlined, freshly isolated B cells will be purified from fresh heparized blood; approximately 70 cc of blood will be drawn from each patient. The B cells will be obtained from the non-rosetting fraction of sheep red blood cell rosetted T-cells, and these B cells will be enriched by panning out the macrophages. Transient transfections will be performed in the identical matter used for the permanent transfections, except that the cells will be immediately (within six hours) reinfused into the same patients at higher doses, e.g., $1\times10^7$ to $1\times10^8$ cells per IV dose. The cells will be able to be injected in an outpatient clinic, since they represent cells from the same patient.

peaks present in the control but missing in the patient are then sequenced, and the peptides synthesized by standard techniques and administered as described above.

Alternatively, B cells or lymphocytes may be transfected with "minigenes" encoding the peptides under the control of an ER translocation signal sequence which would promote the introduction of the peptide into the ER lumen via the normal signal recognition particle dependent secretory pathway. Methods for constructing small peptide encoding "minigenes" have been described (Anderson et al., *J. Exp. Med.* 174:489–492, 1991). The resulting transfected cells may be introduced into the patient by any of the methods described above.

Tolerance to Non-Self Antigens

Tolerance to non-self antigens can be induced by transfecting an HLA class I antigen presenting cell with DNA encoding the protein to which tolerance is to be induced and administering the transfected cells to a patient. This would allow the introduced protein to be artifically incorporated into the tolerance inducing pathway of HLA class I presentation of self peptides; the cell will present peptides derived from the foreign protein by the cellular proteosome complex via the transporter proteins to class I as if they were endogenous, and the cells will induce tolerance to that antigen. This technique can be used to induce tolerance to allograft antigens prior to carrying out the allograft, to inhibit rejection.

Other embodiments are within the following claims.

SEQUENCE LISTING (1) GENERAL INFORMATION:

(iii) NUMBER OF SEQUENCES:1

(2) INFORMATION FOR SEQ ID NO: 1:

(i) SEQUENCE CHARACTERISTICS:
      (A) LENGTH: 9
      (B) TYPE:amino acid
      (C) STRANDEDNESS:
      (D) TOPOLOGY: linear (xi) SEQUENCE DESCRIPTION: SEQ ID NO: 1:

Thr Tyr Gln Arg Thr Arg Ala Leu Val
1

Treatment by Administration of Peptide Antigens

As mentioned earlier, where a defect in class I or one of the genes encoding a protein involved in class I presentation prevents proper presentation of a peptide antigen on the surface of a cell, one strategy is to provide that peptide. The first step in such therapy is to identify the peptide or peptides which are not being presented complexed to class I. This is done by isolating cells from the patient, e.g., peripheral blood lymphocytes, and eluting from the lymphocytes the peptides completed with HLA class I to form an elution profile, according to standard techniques. Such methods are described, e.g., in Madden et al. (1991), Nature, 353:321; Van Bleek et al. (1990), Nature, 348:213; and Rudensky et al. (1991), Nature, 353:622.

The next step is to compare this elution profile to a normal control, to identify the missing peptides in the patient. Those

What is claimed is:

1. A method for inhibiting development in a mammalian subject of a disease characterized by decreased surface expression of MHC class I/peptide complex presentation on the surface of its lymphoid cells in comparison to the lymphoid cells of normal subjects, wherein said decreased surface expression is the result of mutation in a MHC class I gene, the method comprising removing circulating cells from said mammalian subject, transfecting said removed cells with DNA encoding normal, non-mutated MHC class I molecules, whereby said transfected cells express normal, non-mutated MHC class I molecules, and reinfusing said transfected cells into said mammalian subject.

2. A method for inhibiting development of a disease in a mammalian subject characterized by decreased surface expression of MHC class I/peptide complex presentation on the surface of its lymphoid cells in comparison to the lymphoid cells of normal subjects, wherein said decreased surface expression is the result of a defect in or deletion of a peptide transporter gene, said method comprising removing circulating cells from said mammalian subject, transfecting said removed cells with DNA encoding normal, non-defective peptide transporter gene product, whereby said transfected cells express normal, non-defective peptide transporter gene product, and reinfusing said transfected cells into said mammalian subject.

3. A method for inhibiting development in a mammalian subject of a disease characterized by decreased surface expression of MHC class I/peptide complex presentation on the surface of its lymphoid cells in comparison to the lymphoid cells of normal subjects, wherein said decreased surface expression is the result of a defect in or deletion of a gene encoding a component of a proteosome complex, the method comprising removing circulating cells from said mammalian subject, transfecting said removed cells with DNA encoding a normal, non-defective component of the proteosome complex, whereby said transfected cells express normal, non-defective proteosome complex, and reinfusing said transfected cells into said mammalian subject.

4. A method for inhibiting development of an autoimmune disease associated with decreased surface expression of MHC class I/peptide complexes on lymphoid cells of a mammalian subject comprising: removing circulating cells from said mammalian subject, incubating said cells with a substance effective to stimulate MHC class I/peptide complex presentation, and reinfusing said stimulated cells into said mammalian subject.

5. A method according to claim 4, wherein said cells are incubated with a substance selected from the group consisting of beta interferon, gamma interferon, interleukin, and toxoid.

6. A method according to claim 5, wherein said substance is a toxoid selected from pertussis toxoid, BCG, tumor necrosis factor, and diphtheria toxoid.

7. A method according to any one of claims 1, 2, 3 or 4, wherein said cells removed from said mammalian subject are autologous B cells.

8. A method for treating a mammal for an autoimmune disease associated with decreased surface expression of MHC class I/peptide complexes on lymphoid cells of said mammal, wherein said decreased surface expression of MHC class I/peptide complexes is manifested in circulating cells of said mammal which exhibit MHC class I molecules reaching the cell surface that are not complexed with antigen peptide, said method comprising removing circulating cells from said mammal, incubating said cells with antigen peptide until stable MHC class I antigen complexes are formed on the surface of said removed cells, and reintroducing into said mammal said removed cells exhibiting stable MHC class I/peptide complexes on their surface.

9. A method of inhibiting development of an autoimmune disease in a mammalian subject comprising:
(a) determining whether said mammalian subject has a predisposition for developing an autoimmune disease by measuring MHC class I expression on cells of said mammalian subject, a decreased level of MHC class I expression on the surface of said cells indicating such predisposition; and
(b) introducing into said mammalian subject cells expressing normal levels of MHC class I.

10. A method according to claim 9, wherein, in step (b), the mammalian subject is reinfused with autologous cells removed from said subject and treated so as to express normal levels of MHC class I.

11. A method according to claim 10, wherein said autologous cells are autologous B cells of said mammalian subject.

12. A method according to claim 9, wherein said decreased level of MHC class I expression is associated with impaired self antigen presentation.

13. A method according to claim 12, wherein said impaired self antigen presentation is the result of mutation in a MHC class I gene.

14. A method according to claim 12, wherein said impaired self antigen presentation is the result of a defect in or deletion of a peptide transporter gene.

15. A method according to claim 14, wherein said impaired self antigen presentation is the result of impaired function of ATP-dependent transporter protein Tap-1 and/or Tap-2.

16. A method according to claim 12, wherein said impaired self antigen presentation is the result of a defect in or deletion of a gene encoding a component of a proteosome complex.

17. A method according to claim 16, wherein said impaired self antigen presentation is the result of a defect, or deletion, or reduction of expression of a gene encoding LMP-1 and/or LMP-2.

18. A method according to any one of claims 13, 14 or 16, wherein said genetic mutation, deletion or defect is determined using Western blot analysis, mRNA Northern blot analysis, cell surface protein phenotyping, restriction fragment length polymorphism analysis, single-stranded chain polymorphism analysis, denaturing gel electrophoresis, or polymerase chain reaction.

19. A method according to claim 13, wherein, in step (b), the mammalian subject is reinfused with autologous cells removed from said subject and transfected with DNA encoding normal, non-mutated MHC class I molecules, whereby said transfected cells express normal, non-mutated MHC class I molecules.

20. A method according claim 14, wherein, in step (b), the mammalian subject is reinfused with autologous cells removed from said subject and transfected with DNA encoding normal, non-defective peptide transporter gene product, whereby said transfected cells express normal, non-defective peptide transporter gene product.

21. A method according to claim 16, wherein, in step (b), the mammalian subject is reinfused with autologous cells removed from said subject and transfected with DNA encoding the normal, non-defective component of the proteosome complex, whereby said transfected cells express the normal, non-defective proteosome complex.

22. A method according to claim 10, wherein said cells removed from said subject are treated by incubating said cells with a substance effective to stimulate MHC class I presentation.

23. A method according to claim 22, wherein said cells are incubated with a substance selected from the group consisting of beta interferon, gamma interferon, interleukin, and toxoid.

24. A method according to claim 23, wherein said substance is a toxoid selected from pertussis toxoid, BCG, tumor necrosis factor, and diphtheria toxoid.

25. A method according to claim 12, wherein said impaired self antigen presentation is manifested in circulating cells of said mammalian subject which exhibit MHC class I molecules reaching the cell surface that are not complexed with antigen peptides.

26. A method according to claim 25, wherein, in step (b), the mammalian subject is reinfused with autologous circulating cells that are removed from the subject and incubated with antigen peptides to form stable MHC class I antigen complexes on the surface of said cells.

27. The method according to claim 9, wherein said mammalian subject is a human.

28. A method for increasing the level of MHC class I/peptide complex presentation on cells of a subject whose lymphoid cells exhibit decreased surface expression of MHC class I/peptide complex compared to normal lymphoid cells said method comprising removing circulating cells from said subject, incubating said cells with a substance effective to stimulate MHC class I/peptide complex presentation, and reinfusing said stimulated cells into said subject.

29. The method according to claim 28 wherein said cells are incubated with a substance selected from the group consisting of beta interferon, gamma interferon, interleukin, and toxoid.

30. The method according to claim 29 wherein said substance is a toxoid selected from pertussis toxoid, BCG, tumor necrosis factor, and diphtheria toxoid.

31. The method according to claim 28 wherein said cells removed from said subject are autologous B cells.

32. A method for treating a mammal exhibiting a disease associated with decreased surface expression of MHC class I/peptide complexes on lymphoid cells of said mammal, wherein said decreased surface expression is the result of mutation in a MHC class I gene, said method comprising: exposing the immune system of said mammal to correctly associated MHC class I/peptide complexes, wherein said exposing step comprises removing circulating cells from said mammalian subject, transfecting said removed cells with DNA encoding normal, non-mutated MHC class I molecules, whereby said transfected cells express normal, non-mutated MHC class I molecules, and reinfusing said transfected cells into said mammalian subject.

33. A method for treating a mammal exhibiting a disease associated with decreased surface expression of MHC class I/peptide complexes on lymphoid cells of said mammal, wherein said decreased surface expression is the result of a defect in or deletion of a peptide transporter gene, said method comprising: exposing the immune system of said mammal to correctly associated MHC class I/peptide complexes, wherein said exposing step comprises removing circulating cells from said mammalian subject, transfecting said removed cells with DNA encoding normal, non-defective peptide transporter gene product, whereby said transfected cells express normal, non-defective peptide transporter gene product, and reinfusing said transfected cells into said mammalian subject.

34. A method for treating a mammal exhibiting a disease associated with decreased surface expression of MHC class I/peptide complexes on lymphoid cells of said mammal, wherein said decreased surface expression is the result of a defect in or deletion of a gene encoding a component of a proteosome complex, said method comprising: exposing the immune system of said mammal to correctly associated MHC class I/peptide complexes, wherein said exposing step comprises removing circulating cells from said mammalian subject, transfecting said removed cells with DNA encoding a normal, non-defective component of the proteosome complex, whereby said transfected cells express normal, non-defective proteosome complex, and reinfusing said transfected cells into said mammalian subject.

35. The method according to any one of claims 32, 33 or 34, wherein said removed cells are B lymphocytes of the mammalian subject.

36. A method for treating a mammal exhibiting a disease associated with decreased surface expression of MHC class I/peptide complexes on lymphoid cells of said mammal comprising: exposing the immune system of said mammal to correctly associated MHC class I/peptide complexes by obtaining lymphocytes from an individual who is MHC-matched with said mammalian subject but whose lymphocytes exhibit normal MHC class I antigen presentation, irradiating said obtained lymphocytes, and introducing said lymphocytes into the circulatory system of said mammalian subject.

37. The method according to claim 36, wherein the lymphocytes obtained from said individual are B lymphocytes.

38. A method for treating a mammal exhibiting diabetes associated with decreased surface expression of MHC class I/peptide complexes on lymphoid cells of said mammal, wherein said decreased surface expression is the result of mutation in a MHC class I gene, said method comprising: exposing the immune system of said mammal to correctly associated MHC class I/peptide complexes, wherein said exposing step comprises removing circulating cells from said mammalian subject, transfecting said removed cells with DNA encoding normal, non-mutated MHC class I molecules, whereby said transfected cells express non-mutated MHC class I molecules, and reinfusing said transfected cells into said mammalian subject.

39. A method for treating a mammal exhibiting diabetes associated with decreased surface expression of MHC class I/peptide complexes on lymphoid cells of said mammal, wherein said decreased surface expression is the result of a defect in or deletion of a peptide transporter gene, said method comprising: exposing the immune system of said mammal to correctly associated MHC class I/peptide complexes, wherein said exposing step comprises removing circulating cells from said mammalian subject, transfecting said removed cells with DNA encoding normal, non-defective peptide transporter gene product, whereby said transfected cells express non-defective peptide transporter gene product, and reinfusing said transfected cells into said mammalian subject.

40. A method for treating a mammal exhibiting diabetes associated with decreased surface expression of MHC class I/peptide complexes on lymphoid cells of said mammal, wherein said decreased surface expression is the result of a defect in or deletion of a gene encoding a component of a proteosome complex, said method comprising: exposing the immune system of said mammal to correctly associated MHC class I/peptide complexes, wherein said exposing step comprises removing circulating cells from said mammalian subject, transfecting said removed cells with DNA encoding a normal, non-defective component of the proteosome complex, whereby said transfected cells express normal, non-defective proteosome complex, and reinfusing said transfected cells into said mammalian subject.

41. The method according to any one of claims 38, 39 or 40, wherein said removed cells are B lymphocytes of the mammalian subject.

42. A method for treating a mammalian subject exhibiting diabetes associated with decreased surface expression of MHC class I/peptide complexes on lymphoid cells of said mammal comprising: exposing the immune system of said mammalian subject to correctly associated MHC class I/peptide complexes, wherein said exposing step consists essentially of obtaining lymphocytes from an individual who is MHC-matched with said mammalian subject but whose lymphocytes exhibit normal MHC class I/peptide complex presentation, irradiating said obtained lymphocytes, and introducing said lymphocytes into the circulatory system of said mammalian subject.

43. The method according to claim 42, wherein the lymphocytes obtained from said individual are B lymphocytes.

44. A method for treating an autoimmune disease associated with decreased surface expression of MHC class I/peptide complexes in a mammal comprising: intravenous administration of syngeneic or haplotype-matched allogeneic splenocytes or bone marrow cells which express normal levels of MHC class I/peptide complexes on the cell surface, wherein the presence of said syngeneic or allogeneic cells in said mammal inhibits the progression of said autoimmune disease.

45. A method for treating diabetes in a mammal comprising: intravenous administration of autologous splenocytes or bone marrow cells which have been modified ex vivo such that normal levels of MHC class I/peptide complexes are expressed on the cell surface,wherein the presence of said modified autologous splenocytes or bone marrow cells inhibits the progression of diabetes in said mammal.

46. A method of treating an autoimmune disease associated with decreased surface expression of MHC class I/peptide complexes on lymphoid cells of a mammalian subject comprising: removing circulating cells from said mammalian subject, incubating said cells with a substance effective to stimulate MHC class I/peptide complex presentation, and reinfusing said stimulated cells into said mammalian subject.

47. A method for inhibiting development in a mammalian subject of an autoimmune disease associated with decreased surface expression of MHC class I/peptide complexes on lymphoid cells of said subject, the method comprising:

obtaining syngeneic or haplotype-matched allogeneic lymphoid cells which express normal levels of MHC class I/peptide complexes on the cell surface;

removing and isolating said MHC class I/peptide complexes from the surface of said syngeneic or haplotype-matched allogeneic lymphoid cells; and administering to said mammalian subject said isolated MHC class I/peptide complexes.

48. A method for treating a mammal exhibiting a disease associated with decreased surface expression of MHC class I/peptide complexes on lymphoid cells of said mammal comprising:

obtaining syngeneic or haplotype-matched allogeneic lymphoid cells which express normal levels of MHC class I/peptide complexes on the cell surface;

removing and isolating said MHC class I/peptide complexes from said syngeneic or haplotype-matched allogeneic lymphoid cells; and administering to said mammal said isolated MHC class I/peptide complexes.

49. The method according to claim 48, wherein said decreased surface expression is the result of mutation in a MHC class I gene.

50. The method according to claim 48, wherein said decreased surface expression is the result of a defect in or deletion of a peptide transporter gene.

51. The method according to claim 50, wherein said decreased surface expression is the result of impaired function of ATP-dependent transporter protein Tap-1 and/or Tap-2.

52. The method according to claim 48, wherein said decreased surface expression is the result of a defect in or deletion of a gene encoding a component of a proteosome complex.

53. The method according to claim 52, wherein said decreased surface expression is the result of a defect, or deletion, or reduction of expression of a gene encoding LMP-1 and/or LMP-2.

54. A method for treating a mammal exhibiting diabetes associated with decreased surface expression of MHC class I/peptide complexes on lymphoid cells of said mammal comprising:

obtaining syngeneic or haplotype-matched allogeneic lymphoid cells which express normal levels of MHC class I/peptide complexes on the cell surface;

removing and isolating said MHC class I/peptide complexes from said syngeneic or haplotype-matched allogeneic lymphoid cells; and administering to said mammal said isolated MHC class I/peptide complexes.

55. The method according to claim 54, wherein said decreased surface expression is the result of mutation in a MHC class I gene.

56. The method according to claim 54, wherein said decreased surface expression is the result of a defect in or deletion of a peptide transporter gene.

57. The method according to claim 56, wherein said decreased surface expression is the result of impaired function of ATP-dependent transporter protein Tap-1 and/or Tap-2.

58. The method according to claim 54, wherein said decreased surface expression is the result of a defect in or deletion of a gene encoding a component of a proteosome complex.

59. The method according to claim 58, wherein said decreased surface expression is the result of a defect, or deletion, or reduction of expression of a gene encoding LMP-1 and/or LMP-2.

60. A method of inhibiting development of an autoimmune disease in a mammalian subject comprising:

(a) determining whether said mammalian subject has a predisposition for developing an autoimmune disease by measuring MHC class I/peptide complex expression on the surface lymphoid cells of said mammalian subject, a decreased level of surface expression of MHC class I/peptide complex indicating such predisposition; and (b) obtaining syngeneic or haplotype-matched allogeneic lymphoid cells which express normal levels of MHC class I/peptide complexes on the cell surface;

(c) removing and isolating said MHC class I/peptide complexes from said syngeneic or haplotype-matched allogeneic lymphoid cells; and (d) administering to said mammalian subject said isolated MHC class I/peptide complexes.

\* \* \* \* \*